US005811636A

United States Patent [19]

Hanna et al.

[11] Patent Number: 5,811,636

[45] Date of Patent: Sep. 22, 1998

[54] APOMIXIS FOR PRODUCING TRUE-BREEDING PLANT PROGENIES

[75] Inventors: Wayne W. Hanna, Chula; Peggy Ozias-Akins, Tifton, both of Ga.; Michel Dujardin, Philippeville, Belgium

[73] Assignee: The United States of America as represented by the Secretary of Agriculture, Washington, D.C.

[21] Appl. No.: 532,050

[22] Filed: Sep. 22, 1995

[51] Int. Cl.[6] .............................. A01H 5/00; A01H 5/10; C12Q 1/00; C12N 15/29

[52] U.S. Cl. .................. 800/200; 800/250; 800/DIG. 55; 435/6; 47/58; 47/DIG. 1; 536/23.6; 536/24.3

[58] Field of Search .................................... 800/200, 250, 800/DIG. 55; 435/6; 47/58, DIG. 1; 536/23.6, 24.3

[56] References Cited

FOREIGN PATENT DOCUMENTS 8802573 7/1988 WIPO .

OTHER PUBLICATIONS

Adams, S. Apomixis: it could revolutionize plant breeding. Agricultural Research. 41:18–21, 1993.

Welsh and McCelland, *Nucleic Acids Research*, vol. 18(24), pp. 7213–7218 (1990).

Williams et al., Nucleic Acids Research, vol. 18(22), pp. 6531–6535 (1990).

Harlan et al., *Botan. Gaz.*, vol. 125(1), pp. 41–46 (1964).

Asker, S., *Hereditus*, vol. 91, pp. 231–240 (1979).

Scalla et al., *Plant Science Letters*, vol. 22, pp. 269–277 (1981).

Lefbvre et al., "Cytoplasmic Particles Associated with Male Sterility in Faba Bean (*Vicia faba*)", *Breeding and Genetics*, p. 10.

Asker, S., *Hereditus*, vol. 93, pp. 277–293 (1980).

Holl et al., "Genetic Transformation in Plants", *Genetic Transformation*, pp. 301–327.

Taliaferro, C., "Genetic control of Apomixis", pp. 44–47.

Petrov et al., "Transfer of some Elements of Apomixis from Tripsacum to Maize", in: *Apomixis and its Role in Evolution and Breeding*, pp. 9–73 (1985).

Burton, G., *Crop Science*, vol. 29(2), pp. 252–255 (1989).

Fisk and Dandekur, *Scientia Horticulturae*, vol. 55, pp. 5–36 (1993).

Burton, G., *J. of Am. Soc. of Agron.*, vol. 40(10), pp. 908–915 (1948).

Dujardin and Hanna, *J. of Heredity*, vol. 74, pp. 277–279 (1983).

Gonzalez and Hanna, *J. of Heredity*, vol. 75, pp. 317–318 (1984).

Botstein et al., *Am. J. Hum. Genet.*, vol. 32, pp. 314–331 (1980).

Soller and Beckmann, *Theor. Appl. Genet.*, vol. 67, pp. 25–33 (1983).

Hanna et al., *J. of Heredity*, vol. 84(3), pp. 213–216 (1993).

Dujardin and Hanna, *Theor. Appl. Genet.*, vol. 69, pp. 97–100 (1984).

Dujardin and Hanna, *J. Genet. Breed.*, vol. 43, pp. 145–151 (1989).

Lubbers et al., *Theor. Appl. Genet.*, vol. 89, pp. 636–642 (1994).

Ozias–Atkins et al., *Theor. Appl. Genet.*, vol. 85, pp. 632–638 (1993).

Asker and Jerling, *Apomixis in Plants*, pub. CRS Press (1992).

Kindiger and Sokolov, Patent Application P.C. No. 0042.95, "Apomictic Maize".

*Primary Examiner*—David T. Fox
*Assistant Examiner*—Melissa L. Kimball
*Attorney, Agent, or Firm*—M. Howard Silverstein; John Fado; Gail E. Poulos

[57] ABSTRACT

The present invention is directed to cultivated plants that contain the gene(s) from *Pennisetum squamulatum* which express apomixis. More specifically, it relates to apomictic backcross hybrids (BC) that closely resemble pearl millet in morphology and their progeny. These apomictic pearl millets are useful as forage or grain cultivars or used as male pollinators on sexual germplasm to produce new apomictic forage and grain hybrids. The plants can also be used as a source of the gene(s) for controlling apomixis in order to transfer the apomictic mechanism into other cultivated plants to develop true-breeding hybrids.

11 Claims, 10 Drawing Sheets

Preliminary Genetic Map of the "Apomixis" Linkage Group

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

C T G C A G A A G T   G C A G A T C C A A   2 0

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

C T G C A G C A T A   T G G G C T C C T C   2 0

( 2 ) INFORMATION FOR SEQ ID NO:3:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

C T G C A G A C C T   C C A A A C A G   1 8

( 2 ) INFORMATION FOR SEQ ID NO:4:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

C T G C A G C A T G   T G A A C C A T   1 8

( 2 ) INFORMATION FOR SEQ ID NO:5:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

C T G C A G A A C G   A A A C A A G T G T   G   2 1

( 2 ) INFORMATION FOR SEQ ID NO:6:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

G T G T G T C T C T   G A A T C T G G A G   2 0

( 2 ) INFORMATION FOR SEQ ID NO:7:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

C C G C A T C T A C 1 0

( 2 ) INFORMATION FOR SEQ ID NO:8:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

G A G T C T C A G G 1 0

( 2 ) INFORMATION FOR SEQ ID NO:9:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

T G C G G C T G A G 1 0

( 2 ) INFORMATION FOR SEQ ID NO:10:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

C C G A A T T C C C 1 0

( 2 ) INFORMATION FOR SEQ ID NO:11:

( i ) SEQUENCE CHARACTERISTICS:
( A ) LENGTH: 537 base pairs
( B ) TYPE: nucleic acid
( C ) STRANDEDNESS: double ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

```
ACTCNCCATC TGTCGNTCGT NGNCTGTCCC CCCCCTCCCC CACCAGGAAA AAGGGGGATN     60
TACTAAACNT CGNNNTATGG AGTCGANGAA ANNCAAGTTC CTCNCGGAGC TCTTTCAGNT    120
CGCGTCGACT CCGTCGANCG TAGCCGTCGC NCCNCCCCCT CCTCCTNCTG CAGACCTCCA    180
AACAGCACGT CCTCGAGCGC GGCGCGGAGG CCCACCGCGA TGGAACCTCG TCTGTGGAAG    240
CAACGGCGGT AGTGATAACT GCCAGCGGCT TATTTTATTT GTTTCAACAG TCCATGGTTC    300
ACATGCTGCA GACCGNTCGC ATTTTGCCTC TGACAACGAC GGTGCGGCTG CCACTATGGT    360
TATGGTTCAG TACAACCGAA CCATACTCTC CCTCGGTTCG TCCACGGCGG GTGCTCGCAT    420
CACATCACAA CGGATGAATA AAACGGTGTT GGGAGANTNG GTGCTACTCG ATCATGACTT    480
GCTTGGGCAG AACGCATCCG NGTGCTTTAC ATAACCGGAC AAGTTAACTT TTACCGC       537
```

( 2 ) INFORMATION FOR SEQ ID NO:12:

( i ) SEQUENCE CHARACTERISTICS:
( A ) LENGTH: 337 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

```
CTCGATCATC GGGCCTTTGT GATGCTCATG GAGGAGATAT ATTTATAGAG GTAAACATCG     60
AATAAATGGC ATTACTGATG TCCGTAAAAC ATGGATGGGC CCTTAAATGT TGCTGACTGC    120
CCAACTTTTC ACATTGAAGC CCAAACGAGA CAAAAGCTCA GGCCCGTTAA CACTTTCTTT    180
TATAGTGCCC ATTAACACTT TTGGTTGCAA GAACAACCGC ACAAGTGAGA GAAGGAAGGC    240
CAAATTTCAG CTTACACTAC TGGAATCCGT GTCAAGTTCT TACGGCCATT AAAATATTTT    300
ACAGCATCTT TTGTGATATA GTACACGCAG ATCCTAC                             337
```

( 2 ) INFORMATION FOR SEQ ID NO:13:

( i ) SEQUENCE CHARACTERISTICS:
( A ) LENGTH: 537 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:13:

```
GCGGTAAAAG TTAACTTGTC CGGTTATGTA AAGCACNCGG ATGCGTTCTG CCCAAGCAAG     60
TCATGATCGA GTAGCACCNA NTCTCCCAAC ACCGTTTTAT TCATCCGTTG TGATGTGATG    120
CGAGCACCCG CCGTGGACGA ACCGAGGGAG AGTATGGTTC GGTTGTACTG AACCATAACC    180
```

-continued

```
ATAGTGGCAG CCGCACCGTC GTTGTCAGAG GCAAAATGCG ANCGGTCTGC AGCATGTGAA   240

CCATGGACTG TTGAAACAAA TAAAATAAGC CGCTGGCAGT TATCACTACC GCCGTTGCTT   300

CCACAGACGA GGTTCCATCG CGGTGGGCCT CCGCGCCGCG CTCGAGGACG TGCTGTTTGG   360

AGGTCTGCAG NAGGAGGAGG GGGNGGNGCG ACGGCTACGN TCGACGGAGT CGACGCGANC   420

TGAAAGAGCT CCGNGAGGAA CTTGNNTTTC NTCGACTCCA TANNNCGANG TTTAGTANAT   480

CCCCCTTTTT CCTGGTGGGG GAGGGGGGGG ACAGNCNACG ANCGACAGAT GGNGAGT      537
```

( 2 ) INFORMATION FOR SEQ ID NO:14:

( i ) SEQUENCE CHARACTERISTICS:
( A ) LENGTH: 337 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

```
GTAGGATCTG CGTGTACTAT ATCACAAAAG ATGCTGTAAA ATATTTTAAT GGCCGTAAGA    60

SCTTGACACG GATTCCAGTA GTGTAAGCTG AAATTTGGCC TTCCTTCTCT CACTTGTGCG   120

GTTGTTCTTG CAACCAAAAG TGTTAATGGG CACTATAAAA GAAAGTGTTA ACGGGCCTGA   180

GCTTTTGTCT CGTTTGGGCT TCAATGTGAA AAGTTGGGCA GTCAGCAACA TTTAAGGGCC   240

CATCCATGTT TTACGGACAT CAGTAATGCC ATTTATTCGA TGTTTACCTC TATAAATATA   300

TCTCCTCCAT GAGCATCACA AAGGCCCGAT GATCGAG                            337
```

APOMIXIS FOR PRODUCING TRUE-BREEDING PLANT PROGENIES

FIELD OF THE INVENTION

This invention relates to plants that breed true by transferring the apomictic mechanism of reproduction from a wild plant species to a cultivated plant to form a true-breeding hybrid. It also relates to probes for obtaining DNA that controls apomixis, DNA for controlling apomixis, vectors containing the DNA, and to a method for producing true-breeding plant progeny using the DNA.

BACKGROUND OF THE INVENTION

Reproduction in plants is ordinarily classified as sexual or asexual. The term apomixis is generally accepted as the replacement of sexual reproduction by various forms of asexual reproduction (Rieger et al., In Glossary of Genetics and Cytogenetics, Springer-Verlag, New York, N.Y., 1976). Apomixis is a genetically controlled method of reproduction in plants where the embryo is formed without union of an egg and a sperm. There are three basic types of apomictic reproduction: 1) apospory—embryo develops from a chromosomally unreduced egg in an embryo sac derived from the nucellus, 2) diplospory—embryo develops from an unreduced egg in an embryo sac derived from the megaspore mother cell, and 3) adventitious embryony—embryo develops directly from a somatic cell. In most forms of apomixis, pseudogamy or fertilization of the polar nuclei to produce endosperm is necessary for seed viability. These types of apomixis have economic potential because they can cause any genotype, regardless of how heterozygous, to breed true. It is a reproductive process that bypasses female meiosis and syngamy to produce embryos genetically identical to the maternal parent. With apomictic reproduction, progeny of specially adaptive or hybrid genotypes would maintain their genetic fidelity throughout repeated life cycles. In addition to fixing hybrid vigor, apomixis can make possible commercial hybrid production in crops where efficient male sterility or fertility restoration systems for producing hybrids are not known or developed. Apomixis can make hybrid development more efficient. It also simplifies hybrid production and increases genetic diversity in plant species with good male sterility systems.

In sexual reproduction, usually a megaspore mother cell arising from the hypodermal layer of the ovule enlarges and goes through meiosis and two cell divisions to form a linear tetrad of megaspores each with a haploid chromosome number. The three micropylar spores degenerate while the functional chalazal spore enlarges to form an embryo sac with an egg, two polar nuclei, two synergids, and three antipodals.

In apospory, a megaspore mother cell may begin enlarging and even produce chromosomally reduced megaspores but this sexual tissue usually degenerates before embryo sac development. Instead, somatic cells of the nucellus enlarge and the nuclei of these cells go through mitotic divisions to form one to many embryo sacs per ovule each with one to eight chromosomally unreduced nuclei. Aposporous apomicts are characterized by the participation of one or more nucellar cells in the direct formation of one or more embryo sacs. Each nucleus of the aposporous embryo sac has the somatic chromosome number and genotype of the maternal plant. Some aposporous species, pseudogamous apomicts, require pollination and fertilization of polar nuclei for the development of endosperm, but the unreduced aposporous egg develops without fertilization (parthenogenetically). Female meiosis usually is disturbed in aposporous apomicts that form all of their seed asexually (obligate apomicts) so that no functional megaspore continues development beyond the first mitotic division. Facultative apomicts exist in which meiosis and aposporous development occur simultaneously and both reduced and unreduced embryo sacs ultimately reside in the same individual and/or the same ovule. Thus, the two modes of reproduction, sexual and asexual, can coexist or one can be dominant over the other. During obligate apospory, several events must be coordinately regulated, i.e., disturbance or failure of meiosis, aposporous embryo sac development, parthenogenesis; nevertheless only one or a few genes may be responsible for the cascade of events. Some genetic studies, although open to interpretation, suggest that aposporous apomixis is simply inherited (Asker et al., Apomixis in Plants, CRC Press, 1992; Nogler, Embryology of Angiosperms, B. M. Johri, Ed., Springer-Verlag, 475–518, 1984; Winkler, Progr. Rei. Bot., Vol. 2, 293, 1908).

The main difference in diplospory compared to sexual development is that a single megaspore is produced by the megaspore mother cell, and this megaspore has the somatic chromosome number which results in an embryo sac similar in appearance to a sexual embryo sac but with an egg containing the somatic chromosome number.

In adventitious embryony, embryos develop directly from somatic cells of the ovule without formation of embryo sacs. Sexual sacs which are needed for endosperm formation may also form in the same ovule.

Introducing the apomictic trait into normally sexual crops has been attempted. Asker (Heredias, Vol. 91, 231–240, 1979) reports that attempts have been unsuccessful with wheat, sugar beets, and maize. PCT publication WO 89/00810 (Maxon et al., 1989) discloses inducing an apomictic form of reproduction in cultivated plants using extracts from nondomesticated sterile alfalfa plants. The PCT discloses that a soybean hybrid was produced applying this extract to the soybean which was male sterile through the $F_4$generation. The publication further discloses that corn treated with the extract displayed a sterility conversion of 15–26% for seven of the eight genotypes treated. When induction of male sterility was evaluated in sorghum, sunflower, pearl millet, and tomato it was reported that there was reduced seed set in sorghum, pearl millet, and sunflower and reduced fruit set in tomato.

It would be ideal to find genes controlling obligate or a high level of apomixis in the cultivated species and be able to readily hybridize cross-compatible sexual×apomictic genotypes to produce true-breeding $F_1$ hybrids. In reality, most desirable genes controlling apomixis are found in the wild species which are distantly related to the cultivated species. Although interspecific crosses may be possible between the cultivated and wild species, chromosome pairing between genomes is usually low or nonexistent.

Although apomixis is effectively used in Citrus to produce uniform and disease- and virus-free rootstock (Parlevliet J. E. et al., in Citrus. Proc. Am. Soc. Hort. Sci., Vol. 74, 252–260, 1959) and in buffelgrass (Bashaw, Crop Science, Vol. 20, 112, 1980) and Poa (Pepin et al., Crop Science, Vol. 11, 445–448, 1971) to produce improved cultivars, it has not been successfully transferred to a cultivated crop plant. The transfer of apomixis to important crops would make possible development of true-breeding hybrids and commercial production of hybrids without a need for cytoplasmic-nuclear male sterility and high cost, labor-intensive production processes. An obligately apomictic $F_1$ hybrid would breed true through the seed indefinitely and could be considered a vegetative or clonal method of reproduction through the seed. The development of apomictically reproducing cultivated crops would also provide a major contribution toward the food security in developing nations (Wilson et al., IN Proceedings of the International Workshop on Apomixis in Rice, Changsha, People's Republic of China, 13 Jan.–15 Jan., 1992. Hunan Hybrid Rice Research Center, Changsha, People's Republic of China)

The present invention overcomes the problems of the prior art by producing apomictic hybrids of commercial cultivars.

SUMMARY OF THE INVENTION

It is, therefore, an object of the present invention to provide a true-breeding plant which is apomictic by transferring an apomictic mechanism from a wild species to a cultivated plant.

A further object of the present invention is to provide an apomictic hybrid plant that produces progeny identical to itself by transferring an apomictic mechanism from a wild species to a cultivated plant.

It is also an object of the present invention to produce apomictic pearl millet/*Pennisetum squamulatum* hybrids which are more genotypically millet-like.

It is also an object of the present invention to provide aposporous apomictic pearl millet plants which possess at least about 27 to 29 chromosomes.

Another object of the present invention is to provide seed produced by crossing an apomictic cultivated plant with a nurse cultivar as a pollen source for endosperm formation in seeds.

It is another object of the present invention to provide a gene or genes which are responsible for conferring the apomictic trait.

A further object of the present invention is to provide a method for producing hybrid seed by transferring the apomictic mechanism from *Pennisetum squamulatum* to a cultivated Pennisetum plant and crossing the apomictic cultivated plant with a nurse cultivar as a pollen source for endosperm formation in seeds.

Still another object of the present invention is to provide a series of DNA markers for use in assaying cultivated hybrid plants for apomictic reproduction.

It is still a further object of the present invention to provide gene(s) governing and controlling aposporous apomixis, as well as the assignment of the gene(s) to a particular molecular linkage group based upon the association with molecular markers and location the gene(s) to a specific chromosome based upon cytogenetic and molecular investigation.

A still further object of the present invention is to provide a method for conferring the apomictic trait in a plant which normally reproduces by sexual means.

Finally, it is an object of the present invention to provide genetic material which can be manipulated by classical plant breeding methods, cell and tissue culture methods, and/or plant transformation and genetic engineering techniques to introduce the desired gene(s) controlling apomixis into pearl millet as well as additional plant species which can then be clonally selected, regenerated, and propagated to produce individuals capable of aposporous apomictic reproduction.

Further objects and advantages of the present invention will become apparent from the following description.

Deposit of Seeds

Seeds derived from the aposporous apomictic Backcross-6 ($BC_6$), designated E111, were deposited in accordance with the provisions of the Budapest Treaty with American Type Culture Collection, 12301 Parklawn Drive, Rockville, Md. 20852 on Sep. 13, 1995. The Accession number is ATCC 97273.

BRIEF DESCRIPTION OF THE DRAWINGS

FIG. 2 is a photograph of a closeup of inflorescence of E111 showing seed set and intermediate morphological characteristics.

Figure 3:
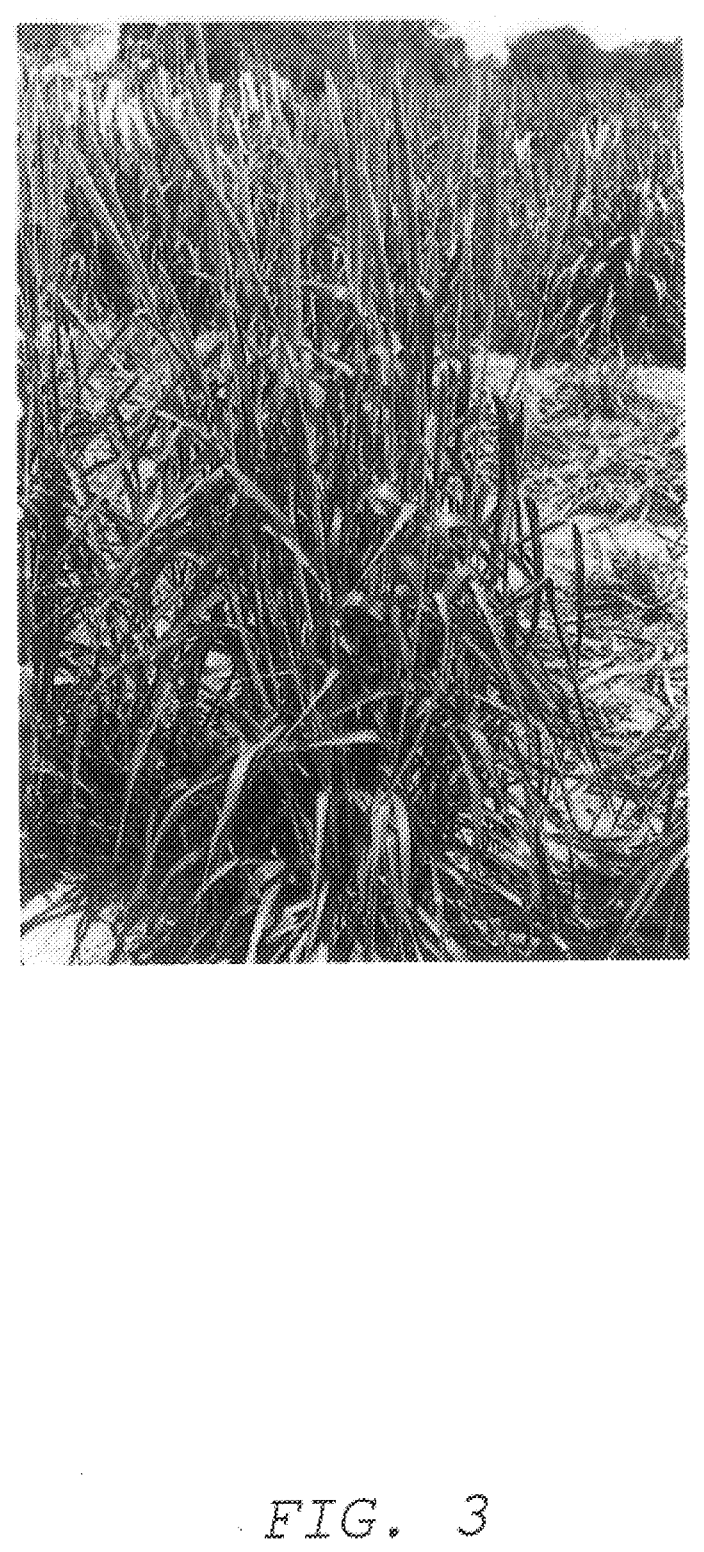

FIG. 3 is a photograph of a closeup of plant E111.

FIG. 4 is a photograph of a closeup of inflorescence of tetraploid (2n=4X=28 chromosomes) cultivated sexual Pearl Millet typical of the recurrent parent in the backcrossing process.

FIG. 5 is a photograph of tetraploid (2n=4X=28 chromosomes) cultivated Pearl Millet typical of the recurrent parent in the backcrossing process.

FIG. 6 is a photograph of a closeup of inflorescence of apomictic *Pennisetum squamulatum* (Tift PS26 or PI319196) with 2n=6X=54 chromosomes which is the donor species for the aposporous apomictic mechanism.

FIG. 7 is a photograph of apomictic *Pennisetum squamulatum* (Tift PS26 or PI319196) with 2n=6X=54 chromosomes which is the donor species for the aposporous apomictic mechanism.

FIG. 8 is a photograph of nine plants of E111 established from seed produced by open-pollination and showing uniform maternal progenies.

Figure 9:
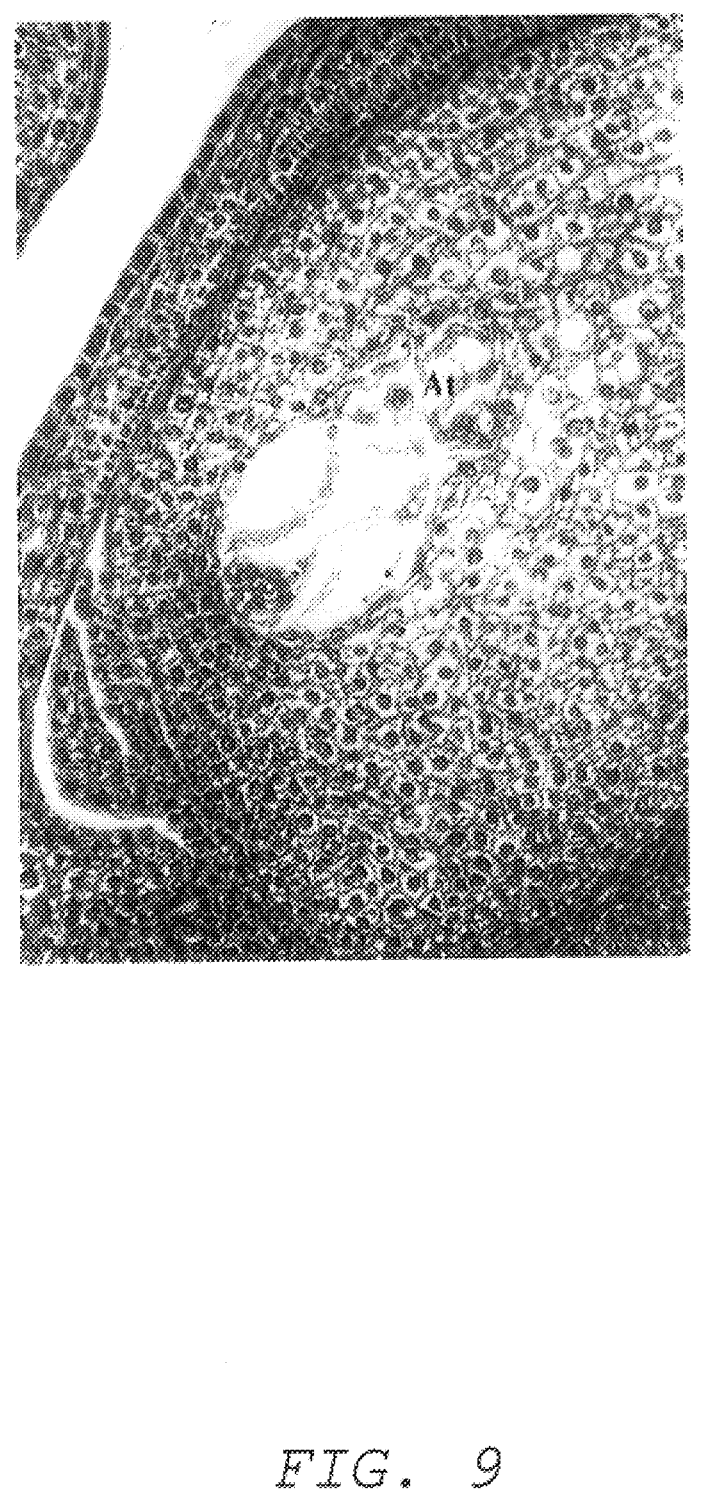

FIG. 9 is a photomicrograph of an ovule from cultivated Pearl Millet typical of the recurrent parent in the backcrossing process. The ovule has one sexual embryo sac. Note antipodal cells (AT) at the top of the embryo sac and "pear-shape" of embryo sac.

DETAILED DESCRIPTION OF THE INVENTION

Figure 1:
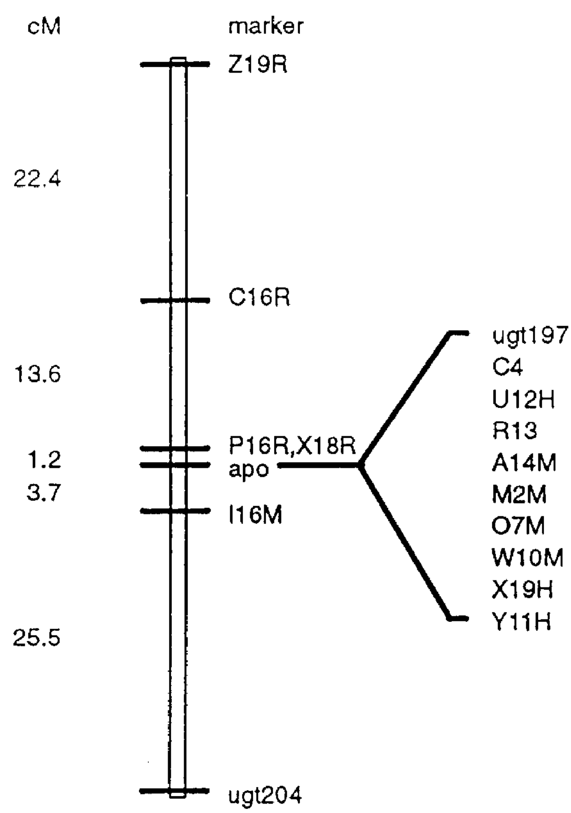
FIG. 1 is a genetic map of the apomixis linkage group.
Figure 10:
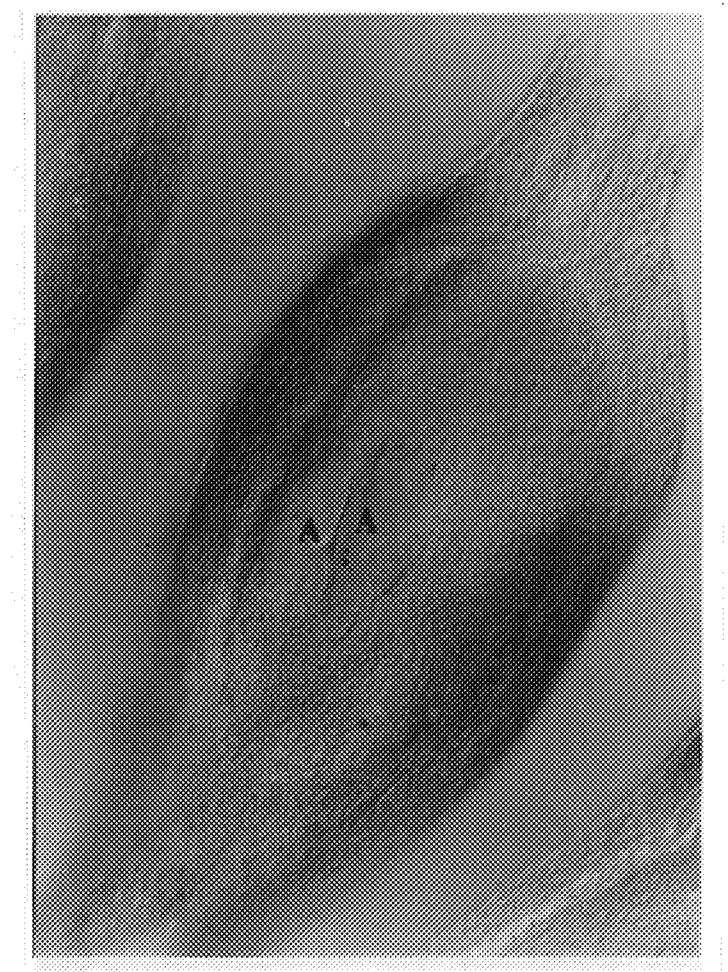
FIG. 10 is a photomicrograph of an ovule from E111 showing two large aposporous apomictic (A) embryo sacs and a small aposporous apomictic embryo sac, all lacking antipodal cells.

In the grass family, Poaceae, tribe Paniceae, the predominant form of apomixis is apospory (Brown et al., Amer. J. Bot., Vol. 45, 253, 1958). The genus, Pennisetum, in which the major cultivated taxon is sexual pearl millet, *P. glaucum* (L.) R. Br., (also referred to as *P. americanum*) contains an abundance of non-domesticated apomictic species (Hanna, Proc. Intl. Pearl Millet Workshop, 33–42, 1986 which is herein incorporated by reference). Transfer of gene(s) controlling apomixis from wild to cultivated species of Pennisetum through crossing has proceeded empirically over the last decade (Hanna, 1986, supra). Interspecific hybrids with pearl millet generally have been highly male sterile. However, some normal male meiosis in an apomictic hybrid, resulting in partially fertile pollen, is a prerequisite for continued crossing since an inherent property of apomixis is the lack of meiotically reduced (i.e. recombinant) female gametes. Progress with introgression has been achieved by elevating male fertility in complex hybrids produced between induced tetraploid pearl millet (2n=4x=28), the wild apomictic species, *P. squamulatum* Fresen (2n=6x=54)

and a third species, *P. purpureum* Schum. (2n=4x=28) (Dujardin et al., J. Genet. Breed. Vol. 43, 145, 1989 herein incorporated by reference).

The aposporous apomictic genetic mechanism has been transferred from a wild species, *Pennisetum squamulatum* (PS) (2n=6x=54), to cultivated sexual pearl millet (PM), *P. glaucum,* at the tetraploid (2n=4x=28) chromosome level. Cultivated pearl millet is usually a sexual diploid (2n=2x=14). Tetraploid sexual pearl millet is used as the recurrent parent in the backcrossing process to transfer the apomictic genetic mechanism because this chromosome level allows maintenance of partial male (pollen) fertility in the backcrossing process. The apomictic mechanism transferred is controlled by dominant gene action, and therefore, has to be transferred through the pollen and requires partial male fertility at each backcross generation. Partial male fertility is also needed for endosperm development to produce a viable seed in the transfer process. Pollen fertility may not be necessary in a commercial aposporous apomictic cultivar since the pollen necessary for endosperm and seed development can be furnished by a 'nurse' cultivar as a pollen source for endosperm formation in seeds (same or possibly different species adjacent to the apomictic hybrid). The 'nurse' cultivar would not affect the genetics of the aposporous apomictic cultivar since the unreduced egg of the cultivar develops parthenogenetically but it would make possible endosperm production.

A partially male fertile aposporous apomictic PM-PS interspecific hybrid is selected in the first generation. When the male fertile PM-PS apomictic hybrid is used to pollinate sexual PM, aposporous-apomictic $BC_1$ plants are found but all are male (pollen) sterile. A male and female fertile sexual pearl millet-napiergrass (PMN) hexaploid (2n=6x=42) is then used as a bridging species to bypass the male sterility barrier. The hexaploid (2n=6x=42) is developed by doubling the chromosome number of a sexual pearl millet (2n=2x=14)×sexual napiergrass (2n=4x=28) male and female sterile interspecific hybrid with 2n=3x=21 chromosomes using colchicine. Partially male fertile apomictic hybrids are obtained when the PMN hexaploids (female) are crossed with a selected apomictic PM-PS hybrid. These partially male fertile apomictic PMN-PM-PS hybrids are referred to as double-cross or trispecific hybrids. An apomictic PMN-PM-PS hybrid is backcrossed to cultivated PM to produce the backcross-1 ($BC_1$) generation. An apomictic partially male fertile $BC_1$ plant is again crossed to PM to produce the $BC_2$ generation. This crossing procedure has been continued through the backcross-6 ($BC_6$) generation. In each generation plants are selected for partial male fertility (viable pollen shed) and apomictic development. In the $BC_4$, $BC_5$ and $BC_6$ generations, plants are also selected for improved seed set. The $BC_4$, $BC_5$ and $BC_6$ plants are partially male fertile, apomictic and morphologically very similar to cultivated pearl millet plants and have 2n=27 to 29 chromosomes.

Double cross hybrids between pearl millet-*P. purpureum* amphiploids and pearl millet-*P. squamulatum* interspecific hybrids proved to be better non-recurrent parents for the recurrent backcross program than $F_1$ interspecific hybrids between pearl millet and *P. squamulatum.* The double cross hybrids have the same chromosome number as the $F_1$ hybrids and approximately the same percentage of the pearl millet chromosomes but produce backcross derivatives that have higher male fertility. Technically, the elimination of both the *P. purpureum* and *P. squamulatum* genomes should not be more difficult than elimination of the *P. squamulatum* alone.

Male fertility is necessary at each generation for transferring apomixis. Both the transfer of apomixis and the elimination of the wild genomes are only feasible through the male gamete because gene(s) controlling apomixis in *P. squamulatum* are dominant. Therefore, one major concern is how pollen fertility would be affected by alien chromosomes in backcross plants. A previous study (Dujardin et al., J. Hered., Vol. 79, 216–218, 1989, herein incorporated by reference) has shown that pollen gametes with more than one extra chromosome are not functional in diploid pearl millet. However, at the tetrasomic level, pearl millet appears to tolerate the addition of *P. squamulatum* and *P. purpureum* chromosomes or the substitution of several of its chromosomes. Partial male fertility in a few backcross plants allows continued backcrossing. Male fertility is expected to improve with further elimination of chromosomes from the wild species.

Another problem related to male fertility is the low number of backcross progeny obtained due to selfing of the female tetraploid pearl millet and partial male fertility of the male pollinator. As the number of backcross generations increases, the probability of obtaining apomictic progeny decreases probably because aneuploid gametes are produced by BC plants with high frequency of pearl millet chromosomes and an alien chromosome with the gene(s) controlling apomixis. Alien or extra chromosomes are usually transferred through the pollen at a reduced frequency. This indicates that genes controlling apomixis in *P. squamulatum* are restricted to a small portion of the genome, possibly to one single chromosome. This agrees with other reports which indicates that apomixis is controlled by one or a few gene(s).

It has not been established prior to this research whether apomixis could be expressed with the same intensity in an advanced backcross plant as in the original apomictic parent. Previous crosses and backcrosses between pearl millet and *Pennisetum orientate* L. C. Rich results in sexual, facultative, and obligate apomictic offspring, depending on the number of haploid sets of chromosomes from both species represented in the backcross plant (Dujardin et al., Crop Sci., Vol. 23, 156–160, 1983). The expression of apomixis in *P. squamulatum* appears less complex. Obligate apomixis is strongly expressed in advanced backcross plants, even though a large part (estimated 90% or more) of the *P. squamulatum* genome has been eliminated.

The apomictic pearl millet-like plants contain the aposporous apomictic mechanism from *P. squamulatum* and produce maternal progenies. The apomictic plants can be used as a source of the gene(s) controlling apomixis. The apomictic mechanism and genes conferring this mechanism can be used to produce apomictic forage and grain hybrids. The techniques for obtaining the gene(s) and introducing it into a plant to induce apomixis may be carried out in the manner known to those skilled in the art. See for example, Fisk et al., Scientia Horticulturae, Vol. 55, 5–36, 1993 which is herein incorporated by reference. Once the gene(s) associated with apomixis is (are) isolated, they can be inserted into plasmids for increase, maintenance, and amplification by known procedures. Several methods are presently known for attempting the insertion of genes into plant and animal material. These range from pollen transformation techniques (Ohta,Y., PNAS, U.S.A., Vol. 83, 715–719, 1986; Smith et al., Plant Science, Vol. 104, 49–58, 1994; deWet et al., International Patent Application WO 85/01856, 1985; all herein incorporated by reference), electroporation techniques (Rhodes et al., Science, Vol. 240, 204–207, 1988; Krzyzk et al., U.S. Pat. No. 5,384,253, 1995; both herein incorporated by reference), and microprojectile gene transfer techniques. Some methods utilize polyethylene glycol mediated systems to assimilate the provided gene into a cell line. Basically, each method is designed for implanting selected genes into the genome of the selected species(Kamo et al., Planta, Vol. 172, 245–251, 1987). Insofar as apomictic reproduction may be under control of either expressed or repressed proteins, as yet to be determined, it may be necessary to introduce appropriate regulatory sequences for appropriate control of expression in the host plant. The microprojectile-mediated gene transfer technique is probably considered the most reliable and effective technique utilized in the industry today. Essentially, multiple copies of the gene to be inserted is placed on any of a variety of projectile mediums (tungsten particles, gold particles, etc.) and inserted into a so-called gene gun. Silicon carbide fibers can also be used to insert multiple copies of the gene. Typically by an infusion of air or pressure system, the particles are projected into a callus of plant tissue. Specific systems for identifying the incorporation of the gene into a callus (also called reporter genes) are the *E. coli* uida "GUS" gene and the green fluorescent protein (GFP) gene from the bioluminescent jellyfish, *Aequoria victoria*. Once transformed cells are identified, they are removed from the callus and transferred to an appropriate growth media. Eventually, through standard tissue culture processes of callus transfer from growth to regeneration media, intact plants are generated. Field studies and progeny testing confirm stable expression of apomictic reproduction and thus incorporation of the appropriate alleles into the genome. Of course other transformation methods could be used as well. Nonlimiting examples of plants that may be used to receive the apomictic gene(s) are those of agronomic and horticultural importance such as grain crops, forage crops, seed propagated fruits, seed propagated ornamentals, and industrial species. Nonlimiting examples of these are pearl millet, corn, wheat, barley, sorghum, rye, oats, rice, beans, peas, soybeans, peanuts, lentils, alfalfa, tomatoes, peppers, tobacco, watermelons, apples, oranges, grapefruit, lemons, limes, onions, beets, turnips, broccoli, cabbage, rape, potatoes, sunflower, flax, mustard, safflower, cotton, etc.

As alluded to above, apomictic reproduction may be under the control of either expressed or repressed proteins. For detecting and identifying these proteins, the protein profile of a non-transformed cell line could be compared with that of a similar transformed cell line. For instance, if the gene(s) for apomixis were implanted into *P. glaucum,* its protein profile could be compared to that of the non-transformed *P. glaucum* by methods well known in the art thereby revealing proteins instrumental in apomictic reproduction. Isolation, elution, and biochemical analysis could be conducted by conventional means.

The present apomictic pearl millet-like plants have 2n=27 to 29 chromosomes. It should be possible to develop the apomictic mechanism at the diploid or disomic level in pearl millet. A polyhaploid with less than one and one-half genomes of the *P. squamulatum* germplasm and only one haploid genome of pearl millet is apomictic (Dujardin et al., Theoretical and Applied Genetics, vol. 72, 33–36, 1986, herein incorporated by reference). This shows that polyploidy (6 sets of chromosomes in *P. squamulatum*) is not necessary for expression of apomixis. Apomixis at the diploid level can be obtained in a number of ways from the present 2n=27 to 29 chromosome material: 1) parthenogenetic development of a rare chromosomally reduced egg, 2) haploids (2n=14) produced from cultured pollen, 3) androgenic development of pollen gamete and 4) haploids from cultured somatic tissue.

Two types of molecular markers dependent on DNA sequence or arrangement have been obtained in order to identify the presence of the apomictic gene in hybrids. One marker is a restriction fragment length polymorphism probe, UGT197, and the other is a random amplified polymorphic DNA (RAPD), (Welsh et al., Nucleic Acids Research, Vol. 18, 7213–7218,1990; Williams et al., Nucleic Acids Research, Vol. 6531–6535, 1990 all herein incorporated by reference) OPC-04. Both markers have been converted to PCR (polymerase chain reaction)-amplifiable sequence-tagged sites (STS). These two markers are unique to the *P. squamulatum* parent and are not found in sexual parents. Furthermore, these markers are not found in sexual backcross plants but are found in backcross apomictic plants. These markers are tightly linked with apomixis and are always present in apomicts.

The present invention is particularly useful for producing true-breeding hybrids which simplifies the production of commercial $F_1$ seed. The present invention also eliminates the need for 1) isolation to produce hybrids and increase female lines; 2) increase and maintenance of large quantities of male sterile, maintainer and restorer lines; and 3) planting large acreages of both male and female parents of a hybrid to produce the commercial hybrid when hybrid seed is only harvested from the female parent. A plant is considered to be an obligate apomict if it produces 100% maternal progenies. A facultative apomict can produce various frequencies of maternal progenies. For the purposes of this application at least 50% or more plants produced by apomixis are useful in hybrid production. Although high levels (above 80%) of aposporous apomictic reproduction are desirable in commercial hybrids (depending on crop species and use), lower levels of aposporous apomictic reproduction could be effectively used to increase production for certain crops and uses. Burton (R. Br., J. Am. Coc. Agron., Vol. 40, 908–915, 1948, herein incorporated by reference) and Burton (Crop Sci., Vol. 29, 252–255, 1989, herein incorporated by reference) showed that 50 to 60% inbred seed in a hybrid population did not reduce forage yields when planted at higher seeding rates as for forage production. The level of apomixis needed in a hybrid would be related to the uniformity needed in the crop species and the seeding rates possible to prevent yield reductions. In developing countries where uniformity is not important and sexual hybrids are expensive to purchase each year, any level of apomixis to increase yield due to hybrid vigor without additional input would be welcomed by the farmer.

Apomixis increases the opportunity for producing superior gene combinations. An obligate apomictic or highly apomictic genotype, regardless of heterozygosity, breeds true. Apomixis broadens the gene pool and lessens the genetic vulnerability of commercial hybrids because one is not limited to females with the male sterility inducing system to produce commercial hybrids.

EXAMPLES

The following examples are intended to further illustrate the invention and are not intended to limit the scope as defined by the claims. Table 1, below is a pedigree for the transfer of the genetic mechanism controlling apomixis in Pennisetum to pearl millet.

TABLE 1

Pedigree of Transfer of Gene Controlling Apomixis in Pennisetum

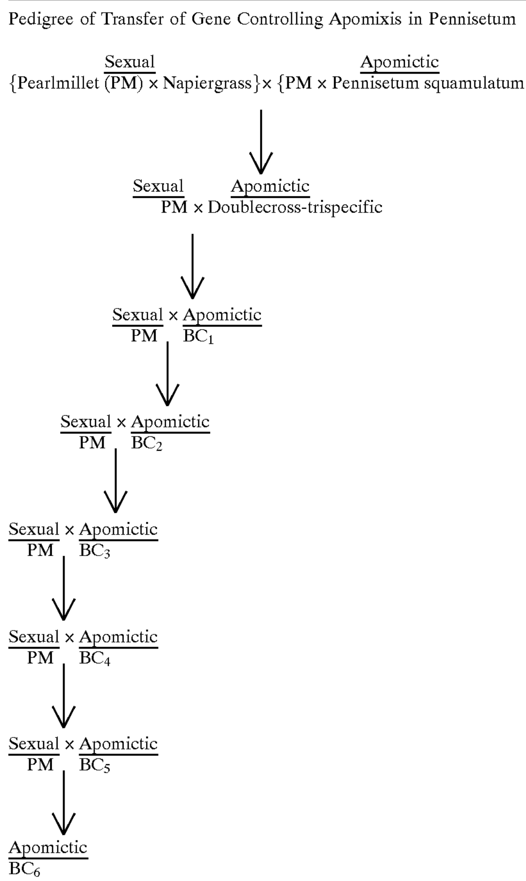

Example 1

The first parent hybrid developed to achieve transfer of the apomictic mechanism from *Pennisetum squamulatum* is an apomictic pearl millet (PM)×*P. squamulatum* cross (Dujardin et al., J. of Heredity, Vol. 74, 277–279, 1983, herein incorporated by reference). One tetraploid 'Tift 239DB' (2n=4x=28) pearl millet inflorescence pollinated with hexaploid apomictic *P. squamulatum* (PI 319196) produced 20 interspecific hybrids. Seeds were germinated in petri dishes at 36° C. and the seedlings were transplanted to 5 cm pots in the greenhouse.

Somatic chromosome counts were made from root tips pretreated for two hours in monobromonapthalene, hydrolyzed for 8 minutes in 5N HCl at room temperature and stained in Feulgens. Inflorescences were fixed in Carnoy's solution for microsporogenesis and in 70% Ethanol:Formaldehyde:Acetic Acid in a ratio of 90:5:5 (FAA) for embryo sac studies. Ovaries were dehydrated in tertiary butyl alcohol, embedded in paraffin, sectioned at 12 um and stained in safranin-fast green.

Pollen fertility was estimated by determining the percent stainable pollen with $I_2KI$. Seed set was determined from inflorescences allowed to open-pollinate in the field.

Although most interspecific hybrids between pearl millet and wild Pennisetum species are reported to be highly male and female sterile, the hybrids produced here are partially fertile. The pearl millet×*P. squamulatum* hybrids closely resemble the male parent in inflorescence characteristics, perennial growth habit, and tillering ability. The hybrids resemble pearl millet in leafinesss and penicillate anther tips. Leaf width and pubescence, photoperiod response and rust resistance varied and were intermediate to both parents. Seventeen of the hybrids were more vigorous than either parent. Three hybrids were very weak and spindly.

The somatic chromosome number in all 20 hybrids is 2n=41 (14 pearl millet chromosomes and 27 *P. squamulatum* chromosomes). Both sexual and apomictic (apospory) reproduction is observed in the interspecific hybrids (Table II, below). Ten hybrids are highly sexual with less than 5% apomictic embryo sacs. Among these hybrids, hybrid 5 shows only sexual embryo sac development. In these hybrids, the functional megaspore forms a mature eight-nucleate embryo sac with one egg nucleus, two synergids, two polars, and three antipodals. At anthesis, the synergids usually disintegrate and antipodals proliferate. Six hybrids are predominantly apomictic. Close examination of megasporogenesis shows that the functional megaspore sometimes degenerates while active nucellar cells develop into mature aposporous embryo sacs. In other ovules, simultaneous development of both a mature sexual embryo sac and multiple aposporous embryo sacs in the same ovule are infrequent. Higher ovule abortion is observed in plants with mainly sexual reproduction. Four hybrids are highly apomictic with less than 5% 8-nucleate sexual embryo sacs. No sexual embryo sacs are observed in hybrid 14. Ten seedlings from open-pollinated apomictic hybrid 12 (SC342-12), have 2n=41 chromosomes and are identical to the seed parent indicating apomictic reproduction.

Endosperm development and multiple proembryos were observed in apomictic ovules. Four twin seedlings were recovered from the open-pollinated progenies that resulted from multiple embryos developing in a single ovule.

Anthers of the 17 interspecific hybrids dehisced at anthesis and shed pollen. Pollen stainability ranges from 29% to 79% (Table III).

Under open-pollination conditions, several hybrids produce viable seeds. Fertility of these hybrids indicate that they are useful for germplasm transfer.

TABLE 2

Embryo sac characteristics of *P. americanum* x *P. squamulatum* interspecific hybrids

| Interspecific hybrids | | Total no. | % Ovales* S. | Ap. | Ap + S | Ab |
|---|---|---|---|---|---|---|
| SC342 | 1 | 149 | 48 | 3 | 0 | 49 |
| SC342 | 2 | 109 | 67 | 3 | 1 | 29 |
| SC342 | 3 | 143 | 5 | 86 | 2 | 7 |
| SC342 | 4 | 129 | 48 | 3 | 0 | 49 |
| SC342 | 5 | 110 | 64 | 0 | 0 | 36 |
| SC342 | 6 | 196 | 68 | 2 | 1 | 29 |
| SC342 | 7 | 109 | 0 | 62 | 1 | 37 |
| SC342 | 8 | 113 | 16 | 72 | 2 | 10 |
| SC342 | 10 | 125 | 1 | 70 | 1 | 28 |
| SC342 | 11 | 105 | 30 | 2 | 0 | 68 |
| SC342 | 12 | 121 | 2 | 92 | 1 | 5 |
| SC342 | 14 | 127 | 0 | 65 | 0 | 35 |
| SC342 | 15 | 122 | 90 | 1 | 0 | 9 |
| SC342 | 16 | 107 | 70 | 2 | 0 | 28 |
| SC342 | 17 | 79 | 72 | 5 | 0 | 23 |
| SC342 | 18 | 121 | 50 | 2 | 0 | 48 |
| SC342 | 20 | 131 | 46 | 1 | 0 | 53 |

*S = sexual, Ap = aposporous, Ab = aborted

TABLE 3

Percent stainable pollen and seed set of *P. americanum* x *P. squamulatum* interspecific hybrids

| Interspecific hybrids | Stainable Pollen % | No. inflores. | OP seed-per-head* |
|---|---|---|---|
| 1 | 50 | 27 | 5 |
| 2 | 30 | 20 | 18 |
| 3 | 53 | 21 | 45 |
| 4 | 70 | 19 | 3 |
| 5 | 69 | 34 | 50 |
| 6 | 57 | 17 | 7 |
| 7 | 31 | 20 | 1 |
| 8 | 29 | 25 | 6 |
| 10 | 57 | 7 | 6 |
| 11 | 50 | 56 | 2 |
| 12 | 70 | 20 | 43 |
| 14 | 66 | 5 | 9 |
| 15 | 68 | 16 | 18 |
| 16 | 79 | 14 | 34 |
| 17 | 60 | 31 | 60 |
| 18 | 39 | 20 | 2 |
| 20 | 53 | 4 | 2 |

*OP = open pollinated

Example 2

In order to bypass the male sterility barrier, a pearl millet, *Pennisetum glaucum,* and Napiergrass, *Pennisetum purpureum* Schaum, cross is produced which is a hexaploid (2n=6x=42) (Gonzalez et al., J. of Heredity, Vol. 75, 317–318, 1984, herein incorporated by reference). The original triploid (2n=3x=21) hybrids were produced using either cytoplasmic-genic male-sterile (cms) inbreds 'Tift 23A' (Tall) or 'Tift 23DA' (Dwarf) pearl millet (2n=14) as the female parent. Diploid (2n=14) cms pearl millet (AA genome) inbreds are pollinated with pollen from tetraploid (2n=28) napiergrass (A'A'BB genomes). Napiergrass clones are highly heterozygous; therefore, a particular cross may give morphologically diverse interspecific hybrids. Six hybrids are selected from crosses Tift 23DA×PI304188, Tift 23DA×UF3245, and Tift 23A×PI388893. Seeds of these crosses are germinated in soil in the greenhouse. Seedlings are transplanted to 5 cm clay pots when they reach an 8 cm height. When plants are 25 cm tall, soil is washed from the roots. The top 10 cm of leaf are clipped from the plant and the roots and crown area immersed in 0.05 percent colchicine for 24 hours. Plants are rinsed in running tap water for 4 hours and replanted in 5 cm clay pots. After 3 weeks, the surviving plants (~30 percent) are transplanted to the field. Induced hexaploids can be identified at anthesis by searching for pollen shedding inflorescences on tillers of the male- and female-sterile triploids. Triploid and hexaploid propagules from a particular clone are isolated, maintained and increased by two node culm cuttings.

Rooted cuttings of a hexaploid clonal pair are transplanted to the field. The hexaploid clones are planted as single plant paired plots with each plant spaced on 2 m centers in a randomized complete block design with 10 replications. Plots are fertilized with 5-10-5 (N-P-K) at 555 kg/ha before planting.

Stomata frequency and length are determined on the last fully expanded leaf (46 days after transplanting) from three tillers in four replications. Leaf impressions are obtained by the cellophane tape method (Sarvella et al., Crop Sciences, Vol. 1, 181–182, 1961, which is herein incorporated by reference). Stomata frequency is obtained from three random measurements per leaf across the center of the blade. Stomatal length is measured on 10 random stomata at each location where frequency is determined.

Flag leaf width and length and stem thickness are determined on five tillers per plant at anthesis. Inflorescence, spikelet and floret characteristics are measured on 15 inflorescences per clone. Plants in all replications are used to measure tillers per plant, plant height, days to flowering, and plant growth rate. Plant growth rate is measured during a two month vegetative growth period beginning one month after transplanting to the field.

Pollen diameter is measured on 150 pollen grains from each clone. Pollen stainability was determined by staining with $I_2KI$.

The hexaploid (6x) clones allow for the determination of polyploidy effects on morphological and fertility characteristics because the clonal pairs are genetically identical (except for random mutations). A number of clones with different genetic backgrounds are also studied, which makes it possible to determine how different genotypes are affected by polyploidy.

The means of the clones for each characteristic measured are summarized in Table IV below. References to significance refers to P=0.05 unless otherwise indicated or shown.

Hexaploids have significantly longer and wider inflorescences, longer florets, higher pollen stainability, larger pollen diameter, and longer flag leaves (except for one genotype when 3x is greater than 6x). These morphological characteristics result in increased size or number due to polyploidy and a differential response is not observed due to plant genotype.

The different responses of the different genotypes indicate that factors other than polyploidy itself appear to affect how a particular morphological character responds to an increase in ploidy. Apparently, the genotype of the plant also determines whether a positive, negative, or neutral response is observed for a particular characteristic. All of the morphological characteristics studied except plant height are quantitatively inherited or controlled by many genes with small effects. Different responses may be expected among the clones depending on the number of genes controlling a certain character and gene action and/or interaction.

Another factor influencing the differential responses of clones is the two-genome nature (AAA'A'BB) of the hexaploid interspecific hybrids. Unpublished results show that the B genome has a dominant effect over the A genome in napiergrass for such genetic characteristics as earliness, inflorescence and leaf characteristics, and seed size.

Pollen stainability and diameter are significantly higher in all clones because at the hexaploid level both the A and the B genomes are balanced (AAA'A'BB) resulting in a more regular meiosis and functional pollen grains.

TABLE 4

Effects of polyploidy on a number of plants morphological and fertility characteristics in pearl millet X napiergrass interspecific hybrids

| | $\bar{X}$ | | t | No. genotypes where: | | |
|---|---|---|---|---|---|---|
| Characteristics | 3X | 6X | test | 3X > 6X | 3X = 6X | 3X < 6X |
| Stomatal frequency, no./mm$^2$ | | | | | | |
| Abaxial epidermis | 129 ± 4 | 118 ± 9 | NS | 1 | 5 | |
| Abaxial epidermis | 104 ± 2 | 95 ± 7 | * | 1 | 5 | |
| Stomatal length, $\mu$m | | | | | | |
| Abaxial epidermis | 41 ± 1 | 46 ± 3 | ** | | 5 | 1 |
| Abaxial epidermis | 41 ± 1 | 45 ± 3 | ** | | 5 | 1 |
| Growth rate, cm/day | 4.4 ± 0.1 | 4.3 ± 0.2 | NS | 1 | 5 | |
| Number tillers per plant | 32 ± 3 | 27 ± 2 | ** | 4 | 1 | 1 |
| Plant height, m | 4.1 ± 0.1 | 3.9 ± 0.1 | ** | 3 | 3 | |
| Stem thickness, cm | 1.7 ± 0.1 | 1.9 ± 0.1 | * | | 2 | 4 |
| Days to flowering | 121 ± 3 | 121 ± 2 | NS | | 6 | |
| Flag leaf width, cm | 1.7 ± 0.1 | 1.7 ± 0.2 | NS | 1 | 2 | 3 |
| Flag leaf length, cm | 16.2 ± 1.9 | 18.6 ± 1.2 | ** | 1 | | 5 |
| Inflorescence length, cm | 19.6 ± 0.1 | 29.8 ± 0.7 | ** | | | 6 |
| Inflorescence width, cm | 1.28 ± 0.6 | 1.45 ± 0.02 | ** | | | 6 |
| Spikelet number per 5 cm | 210 ± 18 | 239 ± 22 | ** | | 3 | 3 |
| Florets per spikelet | 1.3 ± 0.1 | 1.6 ± 0.2 | ** | 2 | 1 | 3 |
| Floret length, cm | 0.39 ± 0.01 | 0.44 ± 0.02 | ** | | | 6 |
| Stainable pollen, % | 2 ± 0.4 | 76 ± 3 | ** | | | 6 |
| Pollen grain diameter, $\mu$m | 29 ± 0.2 | 43 ± 0.8 | ** | | | 6 |

*,**Significant at 0.05 and 0.01 levels, respectively

Example 3

Apomictic trispecific hybrids are obtained by crossing the hybrids made above in examples 1 and 2 (Dujardin et al., Theor. Appl. Genet., Vol. 69, 97–100, 1984, herein incorporated by reference). Eight pearl millet-napiergrass (MN) hexaploids (2n=6x=42) (Tift 23A×PI38893) and two pearl millet-*P. squamulatum* interspecific hybrids (SC342-12, an apomictic hybrid and SC342-17, a sexual hybrid) are used.

The double-cross hybrids, or 'trispecific hybrids' were produced in the greenhouse. The partially exserted inflorescences of the female parent are covered with a glassine bag before stigma exsertion. After the stigmas are exserted, the inflorescences are dusted with pollen from the male parent. Eighteen different crosses, including reciprocals are made (See Table V below).

Seed are germinated in petri dishes at 30° C. and seedlings are transplanted to 5 cm pots in the greenhouse.

Somatic chromosome counts are made from root tips pretreated for two hours in a saturated aqueous solution of monobromnaphthalene, hydrolyzed for 8 minutes in 5N HCl at room temperature and stained in Feulgen reagent. Inflorescences are fixed in Carnoy's solution for examination of microsporogenesis and in FAA for embryo sac studies. Dissected ovaries are dehydrated in tertiary butyl alcohol, embedded in paraffin, sectioned at 12 um and stained in safranin-fast green. Embryo sacs are also observed with a phase-contrast microscope in ovules cleared with methyl salicylate (Crane, PhD thesis, University of Texas, Austin, 1978; herein incorporated by reference).

A minimum of twenty ovules are examined for each double-cross hybrid. Pollen fertility is estimated by determining the percentage of stainable pollen with $I_2KI$. Seed set was determined on inflorescences allowed to open-pollinate in the field.

Crossability is calculated by dividing the number of double-cross hybrids by the total number of plants established in the field and expressing that value as a percentage.

Pearl millet-napiergrass hexaploids (2n=6x=42) pollinated with both sexual and apomictic interspecific pearl millet×*P. squamulatum* hybrids produced 1,940 plants of which 1,730 are identified as double-cross hybrids (89% crossability).

The pearl millet×*P. squamulatum* sexual interspecific hybrid (SC342-17) was pollinated with the MN hexaploid pollen and produced 418 plants of which 402 were identified as double-cross hybrids (96% crossability). Other plants in these crosses resulted from self-pollination of SC342-17 or possibly from facultative apomictic reproduction.

When highly apomictic SC342-12 was pollinated with the MN amphiploids, only morphologically uniform progenies identical to the female hybrid parent (SC342-12) were produced.

All double-cross hybrids were perennial like the interspecific hybrid parents and demonstrated a wide range of variation in vegetative and flowering characteristics. The trispecific hybrids were bushy plants, 3–3.5 m tall, and were intermediate between the two parents in such characteristics as tillering, leaf and stem characteristics, panicle length, density, and shape, number of spikelets per involucre, spiklet size, and bristle length.

Sublethal plants segregated in progenies from seven crosses (Table V below). These sublethal plants had brown leaves and stems. Many died at the seedling stage and were not recorded. Most of the brown plants that were transplanted to the field were weak and grew slowly, but some flowered and a few shed well-stained pollen grains and set seed. Similar sublethal phenotypes were observed previously in triploid pearl millet×napiergrass hybrids.

Somatic chromosome numbers of 2n=41 and 42 were determined for 23 trispecific hybrids. They probably resulted from the union of a 21-chromosome MN gamete (7A+7A'+7B) and a 20- (or 21) chromosome *P. glaucum*×*P. squamulatum* gamete (7A+13S or 14S). The metaphase I (MI) chromosome behavior was observed in four hybrids selected for partial pollen fertility (Table VI below). Meiotic chromosome behavior was similar in all four plants. Chromosomes paired mainly as bivalents with a maximum frequency of 20 bivalents. Trivalents, quadrivalents, and one hexavalent were observed occasionally in pollen of pollen mother cells(PMCs). Similar multivalent associations have been observed intrispecific (*P. glaucum*×*P. purpureum*)×*P. squamulatum* hybrids. At anaphase I (AI), aberrations such as late division of bivalents, unequal separation of multivalents, lagging chromosomes, and chromatic bridges were observed. As many as four micro-nuclei were present in some tetrads. The high frequency of bivalents in the PMCs and the occurrence of multivalents indicated that some homology exists between *P. squamulatum* chromosomes and chromosomes of the pearl millet genome and/or the *P.purpureum* A' or B genome.

Embryo sac development was studied in plants from crosses involving MN hexaploids crossed with sexual and apomictic hybrids between pearl millet and *P. squamulatum.* One population of 64 randomly selected double-cross hybrids between MN1 pollinated by apomictic SC342-12 resulted in 30 obligate apomictic plants, 30 sexual plants, one facultative apomictic plant, and three plants with aborted ovules. No apomictic embryo sac development was observed in 36 plants randomly selected from three crosses between MN1, MN2, and MN4 pollinated with sexual SC342-17 nor in 17 plants from sexual SC342-17 pollinated with MN1. These data indicate that genes for apomixis can be transferred and are expressed in these double-cross hybrids.

Approximately 93% of the double-cross progenies were male-sterile, but several shed pollen with up to 94% stainable pollen. Open-pollinated seed set was determined in 50 male-sterile sexual or apomictic progenies produced from one cross (MN1×SC342-12). The mean seed number per inflorescence was 12.5 in 30 apomictic progenies versus 0.5 in 20 sexual progenies, with a maximum number of 37 for apomictic and 0.8 for sexual plants. Higher seed set in apomictic progenies than in sexual progenies resulted from pseudogamous aposporous embryo sac development. Pollen stainability and seed set in a few partially fertile progenies are summarized in Table VII. The chromosome behavior and pollen stainability data indicate that chromosome irregularity is probably not the only cause of male sterility. Genetic incompatibilities among the genomes of the three species may also contribute to the male sterility.

The pearl millet-napiergrass amphiploids and the pearl millet×*P. squamulatum* interspecific hybrids appear highly cross-compatible and trispecific hybrids can be produced easily. Male- and female-fertility in some of the sexual and apomictic double-cross (trispecific) hybrids allows these hybrids to be used as ‘bridges’ in transferring apomixis and other characteristics from the wild species to pearl millet.

TABLE 5

Percentage of normal and sublethal trispecific plants from pearl millet-napiergrass hexaploids crossed with pearl millet x *P. squamulatum* interspecific hybrids

| | No. of trispecific plants | | |
|---|---|---|---|
| Pedigree* | Total | Normal hybrid % | Sublethal hybrid % |
| MN2xSC342-17 | 353 | 48 | 52 |
| MN1xSC342-17 | 148 | 100 | 0 |
| MN4xSC342-17 | 51 | 0 | 0 |
| MN6xSC342-17 | 0 | 0 | 0 |
| MN2xSC342=12 | 168 | 1 | 99 |
| MN1xSC342-12 | 149 | 100 | 0 |
| MN5xSC342-12 | 222 | 91 | 9 |
| MN6xSC342-12 | 116 | 100 | 0 |
| MN7xSC342-12 | 129 | 100 | 0 |
| MN8xSC342-12 | 396 | 42 | 58 |
| SC342-17xMN2 | 47 | 8 | 92 |
| SC342-17xMN17 | 11 | 100 | 0 |
| SC342-17xMN1 | 24 | 100 | 0 |
| SC342-17xMN4 | 18 | 100 | 0 |
| SC342-17xMN5 | 17 | 88 | 12 |
| SC342-17xMN7 | 94 | 100 | 0 |
| SC342-17xMN8 | 191 | 17 | 83 |
| SC342-12xMN17 | 0 | 0 | 0 |

*MN = pear millet-napiergrass hexaploid; SC = pearl millet x *P. squamulatum* interspecific hybrids

TABLE 6

Mean Number of chromosome associations at diakinesis and metaphase I in trispecific hybrids between pearl millet-napiergrass hexaploids and pearl millet x *P. squamulatum* interspecific hybrids

| Trispecific* hybrid no. | Pedigree | 2n chromosome no. | Pollen stainability % | No. PMCs observed | Chromosome Associations I $\bar{X}$ | II | III | IV |
|---|---|---|---|---|---|---|---|---|
| H128-2(S) | SC342-17xMN1 | 42 | 83 | 8 | 94.34 (0–11) | 16.51 (12–20) | 0.61 (0–2) | 0.64 (0–3) |
| H278-8(Ap) | MN1xSC342-12 | 42 | 35 | 79 | 9.90 (3–18) | 14.41 (9–18) | 0.33 (0–2) | 0.44 (0–2) |
| H282-6(S) | MN7xSC342-12 | 41 | 40 | 102 | 4.90 (1–11) | 17.67 (13–20) | 0.29 (0–2) | 0.23 (0–2) |
| H282-5(Ap) | MN7xSC342-12 | 42 | 12 | 83 | 6.89 (1–13) | 14.42 (9–19) | 0.61 (0–3) | 0.86 (0–3) |

TABLE 7

Percentage stainable pollen and seed set in partially malefertile progenies from crosses between pearl millet-napier-grass hexaploids and pearl millet x *P. squamulatum* hybrids

| Trispecific progenies | Reproductive behavior | Stainable pollen % | No. inflores-cences | No. seed per OP* inflorescence |
|---|---|---|---|---|
| H280-2 | Apomict | 51 | 19 | 9 |
| H280-5 | Sexual | 47 | 8 | 0 |
| H280-6 | Sexual | 48 | 8 | 16 |
| H282-5 | Apomict | 12 | 21 | 7 |
| H282-6 | Sexual | 40 | 14 | 12 |
| H283-3 | Apomict | 73 | 36 | 13 |

*OP = open-pollinated

Example 4

Apomixis is more easily transferred through the male gamete. Therefore, progress in interspecific transfer of apomixis depends to a large extent on the production in each generation of apomictic hybrid derivatives that are partially male fertile (Dujardin et al., J. Genet. & Breeding, Vol. 43, 145–151, 1989, herein incorporated by reference). Tetraploid (2n=4x=28) pearl millet inbred lines Tift 23BE, Tift 239, or Tift 23BE×Tift 239DB hybrids are used as recurrent female parents. Tetraploid cytoplasmic-nuclear male sterile (cms) pearl millet developed by crossing tetraploid cms inbred line Tift 23AE with tetraploid inbred line Tift 239DB is used as the female for testing the viability of pollen from backcross plants. Tetraploid pearl millet line Tift 23 with a red dominant marker was used as pollen parent in test crosses. Hybrids used as the male. parent to produce backcross-one include three double cross hybrids (H280-2, H282-3, H282-5) (2n=42) from crosses between pearl millet×*P. purpureum* amphiploids crossed with pearl millet× *P. squamulatum* interspecific hybrids described above in example 3 (Dujardin and Hanna, Theor, Appl. Genet., Vol. 69, 97–100, 1984, herein incorporated by reference). The hybrids or backcross derivatives, as well as those obtained from each cycle, are selected for both obligate apomixis and pollen fertility. Plants are screened first for male fertility.

Panicles at one day before anthesis are collected to study embryo sac development. Part of the inflorescence is fixed in FAA for 24 hours and stored in 70% ethanol. Embryo sacs are observed with a phase contrast microscope in ovules cleared with methylsalicylate (Young et al., Can. J. Bot, Vol. 57, 1668–1672, 1979, herein incorporated by reference). Pollen fertility is estimated by determining stainability in a 2% $I_2KI$ solution. Selfed seed set is determined on panicles that had been enclosed in glassine bags before stigma exsertion. Open-pollinated seed from apomictic and male fertile plants are harvested for further evaluation in progeny tests. Somatic chromosome counts are made from root tips pretreated for 2 hours in monobromonaphthalene, hydrolyzed for 8 minutes in 5N HCl at room temperature and stained in Feulgen solution. Young panicles are fixed in Carnoy's solution for examination of meiotic chromosomes in pollen mother cells.

Crosses between tetraploid (2n=28) pearl millet and three obligate apomictic-male fertile double cross hybrids (DCH) selections, described above in example 3, resulted in 1200 $BC_1$ progenies. One $BC_1$ plant (M148), that exhibits morphological characteristics intermediate between *P. glaucum* and a DCH was selected for its excellent pollen shed (45% stainable pollen). Cytological observations of embryo sacs in ovules and progeny tests indicated that M148 was unquestionably an obligate apomict. This plant and 30 of its open pollinated progeny have 36 chromosomes. The pollen collected from M148 was used to pollinate tetraploid pearl millet. Crosses gave rise to 7,000 offspring which were space-planted in the field. More than 95% of these plants were pearl millet selfs. Three hundred plants were identified as $BC_2$ based on their morphological characteristics. Among these, 78 reproduce by obligate apomixis and 8 are, in addition, male fertile. Pollen stainability in the most fertile $BC_2$ plants is 28%. Somatic chromosome numbers range from 2n=29 to 35 in 37 $BC_2$ derivatives.

Nineteen thousand progeny from tetraploid pearl millet× $BC_2$ hybrids were evaluated. Most resulted from selfing of pearl millet. As the number of backcross generations increase, the separation of backcrosses from pearl millet selfs becomes more difficult because of less distinctive morphological differences. In addition, the plant phenotype gives no indication of its method of reproduction.

Therefore, screening this large population of individuals is the only way of finding an apomictic backcross derivative. Aposporous embryo sac development in ovules is used to detect apomictic backcross plants. One backcross-three ($BC_3$) that shed pollen and showed apomictic reproduction was selected from 1053 progeny that were analyzed cytologically.

The $BC_3$ hybrid (K169-46) is an annual and vigorous bunchgrass, 1.5 m tall. It differs from pearl millet by producing more tillers and panicles per plant, and having thinner stems and narrower leaves, and longer and fewer dense panicles. K169-46 has 29 somatic chromosomes, which are similar to those of pearl millet. As the three species involved in the original cross had several chromosomes similar in morphology and size to those of pearl millet, the number of chromosomes from each respective species in K169-46 is unknown. Theoretically, the alien chromosomes should represent less then 10% of the K169-46 genome. Meiotic chromosome behavior was irregular. Metaphase I chromosomes remained as univalents, bivalents, trivalents, quadrivalents, or associated pentavalents (Table VIII below). At least five chromosomes remained unpaired in all microsporocytas, suggesting those are from *P. squamulatum* and/or *P. purpureum*. Trivalents and quadrivalents are observed in 88% and 55% of the pollen mother cells, respectively. Chromosome segregation at anaphase I is irregular, resulting in diads with 11 to 16 chromosomes. Up to three laggards were recorded at anaphase I. Pollen grains are variable in size and 37% contain dense cytoplasm. Pollen grains of K169-46 are observed adhering to the stigmas of tetraploid pearl millet after pollination and many of them germinate. K169-46 sheds abundant pollen in the field.

Embryo sac development was observed in 110 ovules of K169-46. Multiple embryo sacs developed from active nucellar cells in 97% of ovules, while 3% were aborted. No meiotically reduced 8-nucleate embryo sacs were observed in immature ovules. The number of embryo sacs per ovule ranged from 1 to 7. Most ovaries continued to grow for some time after anthesis regardless of whether they eventually produce mature caryopses. Failure of endosperm development contributed to low set of mature seed. K169-46 produced seed under self- and open-pollination. Seed set, however, was higher after pollination with pollen from tetraploid pearl millet (Table IX below) and was generally higher on the first panicles developed.

Obligate apomictic reproduction of K169-46 was confirmed by a progeny test in which 306 offspring were phenotypically uniform and identical to K169-46. After pollination by pearl millet with a red dominant marker, all progenies obtained were green plants with maternal appearance. Two off-types, however, were found among 60 progenies obtained from another cross between K169-46 and tetraploid pearl millet. The first off-type was a small variant of K169-46, 30 cm tall, that had 29 chromosomes similar to K169-46. This off-type, morphologically identical to K169-46, except for height, probably arose from a mutation. The second off-type was almost identical to tetraploid pearl millet and had 43 chromosomes. It supposedly had the complete chromosome complement of K169-46 plus 14 chromosomes from the reduced complement of tetraploid pearl millet. This plant was highly sterile. Multiple four-nucleate embryo sacs were observed in both off-types, indicating they were obligate apomicts.

Pollination of 4 cms tetraploid pearl millet infloresences with pollen of K169-46 in the green house gave rise to 2.3% seed set and 30 seedlings. Other crosses made on 13 inflorescences in the field, produced 3.4% seed set and 76 seedlings. By comparison, the same inflorescences of cms tetraploid pearl millet pollinated with male fertile tetraploid pearl millet had 60.9% seed set. These results indicated that pollen from K169-46 was capable of fertilizing eggs of tetraploid pearl millet, but a low percentage of pollinations resulted in mature seed, probably due to imbalanced gametes resulting from meiotic irregularities in K169-46.

TABLE 8

Meiotic chromosome association * in a $BC_3$ derivative (2n = 29) from a double cross hybrid between pearl millet-*P. purpureum* amphiploid and pearl millet *P. squamulatum* interspecific hybrid

| | Metaphase I chromosome associations[b] | | | | |
|---|---|---|---|---|---|
| | I | II | III | IV | V |
| Mean | 9.33 | 5.86 | 1.74 | 0.65 | 0.02 |
| Range | (5–13) | (2–10) | (0–6) | (0–3) | (0–1) |

*I, univalent; II, bivalents; III, trivalents; IV, quadrivalents; V, pentavalents.
[b]Recorded on 106 pollen mother cells.

TABLE 9

Percent seed set on K169-46, a $BC_3$ derivative (2n = 29) from a double cross hybrid between a pearl millet-*P. purpureum* amphiploid and a pearl millet-*P. squamulatum* interspecific hybrid

| Lines or cross | No. of florets | Seed set (%) |
|---|---|---|
| Selfed K169-46 | 1020 | 4.1 |
| Open pollinated K169-46 | 1235 | 6.4 |
| K169-46 x tetraploid pearl millet | 1020 | 13.2 |

Example 5

The $BC_3$ clonal line K169-46 and the four parents(or three species) appearing in its pedigree (Table 1) are the genotypes used to initiate a search for molecular markers potentially linked with apomixis (Ozias-Akins et al., Theor, Appl. Genet., Vol. 85, 632–638, 1993, herein incorporated by reference). Two types of molecular markers dependent on DNA sequence or arrangement are applied in the linkage study: restriction fragment length polymorphisms (RFLP) (Botstein et al., Amer. J. Hum. Genet., Vol. 32, 314–331, 1980; Soller et al., Theor. Appl. Genet., Vol. 67, 25–33, 1983; Tanksley et al., Bio/Tech, Vol. 7, 257–264, 1989; all herein incorporated by reference) and random amplified polymorphic DNAs (RAPD) (Welsh et al., Nucleic Acids Res., Vol. 18, 7213–7218, 1990; Williams et al., Nucleic Acids Res., Vol. 18, 6531–6535, 1990; all herein incorporated by reference).

All genotypes contributing to the pedigree of $BC_3$ and the $BC_3$ clonal line are used for DNA isolation. These genotypes include pearl millet inbred lines '23BE' and '239DB', *P. purpureum* accession PI388893, and apomictic *P. squamulatum* accession PS26. $BC_4$ plants were raised from seed produced by crossing male-sterile tetraploid pearl millet with $BC_3$from example 4 above (Dujardin et al., J. Genet. Breed., Vol. 43, 145–151, 1989, supra). The male-sterile female parent insured that backcrosses, and not selfed progeny, were obtained. Sixty-six male-sterile $BC_4$s were screened for embryo sac development by clearing ovules in methylsalicylate as described above in example 4. To supplement the number of apomicts, ten apomictic $BC_4S_1$ ($S_1$=first selfed generation from $BC_4$) progeny from four previously classified male-fertile apomictic $BC_4$ plants, one $BC_4S_1$ male-sterile plant, and 33 segregating progeny (14 sexual, 4 obligate apomicts, 15 facultative apomicts) from one previously identified male-fertile $BC_4$facultative apomict (designated A1), were included in the analysis. Tender furled leaves were harvested from the above plant materials, then frozen and stored at −80° C.

A method modified from Tai et al. (Plant Mol. Biol. Rep., Vol. 8, 297–303, 1990 herein incorporated by reference) is used for DNA extraction. Approximately 10 grams of frozen tissue is ground to a fine powder with liquid nitrogen then added to 75 ml of extraction buffer consisting of 100 mM Tris-HCl, pH 8.0; 50 mM EDTA, 500 mM NaCl, 1.25% SDS, and 0.38% sodium bisulfite added just before use. The homogenate is incubated at 65° C. for 20–60 minutes and subsequently processed according to the published protocol. Genomic DNA is digested with DraI, HindIII, EcoRI, EcoRV, or BamHI, electrophoresed in an 0.8% agarose gel in Tris-borate-EDTA buffer, and transferred to nylon membranes (Magnagraph, Genescreen Plus) by the capillary method of Southern (J. Mol. Biol., Vol. 98, 503–517, 1975; herein incorporated by reference). Blots were prehybridized and hybridized according to the respective manufacturers' instructions using aqueous hybridization solutions at 65° C. PCR-amplified or gel-purified plasmid inserts are labeled with $^{32}P$ by the random hexamer method. Hybridized blots are washed at a final stringency of 0.1×SCC, 65° C.

For library construction, DNA from $BC_3$ is digested with PstI and ligated with PstI-cut pUCl9. Plasmid DNA is transformed into host strain DH5α and recombinant clones are selected for ampicillin resistance and inactivation of lacZ by white colony formation on media containing bluo-gal. Approximately 90% of the PstI clones were single to low copy number as judged by hybridization with $^{32}P$-labelled total genomic DNA from pearl millet.

For DNA sequencing, plasmid inserts are amplified with M13 forward and reverse primers (New England Biolabs) and purified by HPLC prior to sequencing. Purified insert DNA is sequenced using the DyeDeoxy Terminator Sequencing Kit and automated sequencing equipment from Applied Biosystems. Sequencing primers are nested M13 forward and reverse sequences. Sufficient sequence is generated to allow the design of oligonucleotide primers that would amplify sequence-tagged sites (STS) from genomic DNA.

For DNA amplification, forward and reverse oligonucleotide primers for sequence-tagged sites are synthesized by the Molecular Genetics Facility, University of Georgia as follows:

| | | |
|---|---|---|
| UGT184f | 5' CTGCAGAAGTGCAGATCCAA 3' | SEQ ID NO 1 |
| UGT184r | 5' CTGCAGCATATGGGCTCCTC 3' | SEQ ID NO 2 |
| UGT197f | 5' CTGCAGACCTCCAAACAG 3' | SEQ ID NO 3 |
| UGT197r | 5' CTGCAGCATGTGAACCAT 3' | SEQ ID NO 4 |
| UGT1f1 | 5' CTGCAGAACGAAACAAGTGTG 3' | SEQ ID NO 5 |
| UGT1r2 | 5' GTGTGTCTCTGAATCTGGAG 3' | SEQ ID NO 6 |

Amplification conditions in a Perkin Elmer/Cetus thermal cycler were denaturation for three cycles of 1 minute at 97° C. and 32 cycles of 1 minute at 94° C., annealing for 1 minute at 45° C. (UGT197) or 55° C. (UGT184,UGT1), and extension for 2 minutes at 72° C. with a 3 second auto-segment extension of each cycle. RAPD primers are obtained as kits of 20 10-base primers (Operon Technologies, Alameda, Calif). Primer kits B,C,D,E,and F were surveyed. Amplification conditions are essentially according to Williams et al. (supra) except that primer concentration is increased to 0.5 uM. The PCR reaction mix (25 ul) contains 10 mM of Tris-HCl, pH 8.3; 50 mM KCl, 1.5 mM $MgCl_2$, 0.1% Triton X-100, 100 um each of dATP, dCTP, dGTP, dTTP, 0.5 uM primer, 25 ng genomic DNA, and 0.5 U of Taq DNA polymerase (Promega). Amplification conditions consisted of three cycles of 1 minute at 97° C., 1 minute at 36° C., 2 minute at 72° C. with a 3 second auto-segment extension of each cycle.

Over 90% of the 48 RFLP probes were single to low copy number as judged by hybridization with genomic DNAs. Approximately 94% of the probes were polymorphic between *P. glaucum* and *P. squamulatum.* Seven out of forty-eight RFLP probes hybridized to a restriction fragment in $BC_3$ that was shared only with the apomictic parental accession of *P. squamulatum.* One of the informative probes (UGT197) was particularly interesting because it did not hybridize at all with non-apomictic genotypes in the pedigree of $BC_3$. Three of the probes (UGT197, UGT184, UGT1) were converted to sequence-tagged sites by amplification of the expected fragments of 144 bp, 181 bp, and 1 kb respectively, from $BC_3$genomic DNA. Two unpredicted results were also obtained from DNA amplified with the UGT197 and UGT184 oligonucleotide primers. First, a RAPD pattern was observed when three of the four primers were used individually in an amplification reaction and second UGT184 forward+reverse primers amplified a band from *P. purpureum* that appeared to be indistinguishable from the band amplified in *P. squamulatum* and $BC_3$. Even though UGT184 was amplified in parental *P. purpureum,* the UGT184-probed genomic Southern indicated that only the *P. squamulatum* marker was present in $BC_3$. One-hundred RAPD primers were surveyed for their ability to amplify informative fragments. Twenty-six of the primers resulted in essentially no amplification. Of the remaining 74 primers, all amplified one or more polymorphic bands between *P. glaucum* and *P. squamulatum.* Only four primers:

| | | |
|---|---|---|
| OPC-04 | 5' CCGCATCTAC 3' | SEQ ID NO 7 |
| OPE-11 | 5' GAGTCTCAGG 3' | SEQ ID NO 8 |
| OPE-14 | 5' TGCGGCTGAG 3' | SEQ ID NO 9 |
| OPF-05 | 5' CCGAATTCCC 3' | SEQ ID NO 10 |

amplified clearly distinguishable and reproducible fragments that were shared solely by $BC_3$ and *P. squamulatum.* Several additional primers amplified fragments shared by *P. purpureum, P. squamulatum,* and $BC_3$. This result might indicate a closer relationship between *P. purpureum* and *P. squamulatum* than had previously been suggested. It also complicated the molecular analysis by reducing the number of potentially informative markers.

Mendelian segregation can not be established from any of the backcross populations because the chromosome bearing the gene(s) for apomixis is from an alien genome and presumably does not have a homolog with which to pair regularly in $BC_3$ (Dujardin et al., J. Genet. Breed., Vol.43, 145–151, 1989). The frequency of transmission of apomixis in these progeny is known to be low (Dujardin et al., 1989, supra) and the possibility for recombination is unknown. Because of these limitations, the usual statistical analysis of molecular data in the backcross population could not be relied on. Instead linkage can be assumed if a molecular marker phenotype and reproductive phenotype correspond at least 95% of the time.

Segregation of seven informative molecular markers (four RAPD and three STS markers) was followed in the male-sterile $BC_4$ population. A male-sterile female parent was chosen to generate the $BC_4$ population for molecular analysis so that the hybrid nature of all backcross progeny would be assured and would eliminate the possibility of selfs. This strategy is not useful, however, for perpetuating a backcrossing program since all $BC_4$ individuals would be male-sterile and could not be used as male parents to advance to the $BC_5$ generation. In an obligate apomict, recombination occurs only during male gametogenesis; thus far transfer of apomixis must occur through the pollen and not through the unreduced, maternally-derived egg. Sixty-six male-sterile $BC_4$ progeny were screened for mode of reproduction by examining cleared ovules and scoring embryo-sac development. Sixty-one reproduced sexually, two were obligate apomicts, and the remaining three showed some ambiguity in embryo sac development and so were classified as facultative apomicts. Based on the segregation of the seven PCR-based markers, it appears that there are at least two independently assorting linkage groups in $BC_3$ that were derived from *P. squamulatum* (Table X below). One of the linkage groups, identified by cosegregation of five of the molecular markers (OPE-11, OPE-14, OPF-05, UGT184, UGT1), was transmitted to 43% of the male-sterile $BC_4$ progeny regardless of reproductive mode (Table X). One individual ($BC_4$-9) lacked three of five markers (OPF-05, UGT184, UGT1) and one ($BC_4$-109) lacked the other two of five markers (OPE-11, OPE-14) indicating loss through recombination or chromosome breakage. Strict cosegregation of the remaining two markers (UGT197, OPC-04) did occur (Table X). These markers are tightly linked with apomixis and are always present in obligate apomicts. Only one ($BC_4$-109) out of 61 sexual, male-sterile $BC_4$ progeny had both markers for apomixis. Three explanations could account for this observation: the plant collected was mislabelled or misclassified, expression of the gene(s) for apomixis was somehow attenuated in this individual, or chromosome breakage separated the markers from the gene(s) for the trait.

None of the 14 sexual male-fertile A1 ($BC_4S_1$) individuals had the markers for apomixis, while the four obligate apomicts from this population all carried the markers. The markers for apomixis were present in 72% of the individuals from two populations classified as facultative apomicts. Although this result might indicate that apomixis occurs in individuals lacking the markers, this conclusion should be reserved until a better method is developed for categorizing facultative apomicts.

TABLE 10

Amplification of the five informative markers in Pennisetum parental genotypes and $BC_4$ and $BC_4S_1$ progeny. Sexual (S) plants comprise four possible genotypes, two of which are rare and occur in only one plant each. Facultative (F) apomicts do not display a consistent genotype, but the ambiguity in classification prevents any definite conclusions. Obligate apomicts (A) always have the linkage group represented by OPC-04 and UGT197, and are variable for presence of the second linkage group

| | | Marker | | | | |
|---|---|---|---|---|---|---|
| Individuals | Reproduction | OPE-11 OPE-14 | UGT1 | OPF-05 | UGT184 | UGT197 OPC-04 |
| Parental genotypes | | | | | | |
| 23BE | S | − | − | − | − | − |
| 239DB | S | − | − | − | − | − |
| N39-2 | S | − | − | − | + | − |
| PS26 | A | + | + | + | + | + |
| $BC_3$ | A | + | + | + | + | + |
| Male-sterile $BC_4$ progeny | | | | | | |
| 1,2,7,8,12,13,25,26,29,30,32,35–37, 39,44,54,56,65,79,80,83,86,88,90 92–94,101,102,114,119 | S | − | − | − | − | − |
| 3,41,48 | S | − | + | − | − | − |
| 5,10,11,14,19–22,28,38,40,43,45,47, 50,52,58,61,97,100,110 | S | + | + | + | + | − |
| 49,51,91 | S | + | − | + | + | − |
| 9 | S | + | − | − | − | − |
| 109 | S | − | + | + | + | + |
| 42 | F | − | − | − | − | + |
| 59,118 | F | + | + | + | + | − |
| 53 | A | + | + | + | + | + |
| 84 | A | − | − | − | − | + |
| $BC_4S_1$ apomictic progeny | | | | | | |
| A1-4,81,11,14 | A | − | − | − | − | + |
| A4-3,4,9 | A | − | − | − | − | + |
| A10-1 | A | + | + | + | + | + |
| A21-7,11,28 | A | − | − | − | − | + |
| A25-1,8,10,12 | A | − | − | − | − | + |

Example 6

This example demonstrates the utility of the two probes of example 5 above by demonstrating that other Pennisetum species carry the molecular markers shown to be linked to apomixis (Example 5 above) (Lubbers et al., Theor. Appl. Genet., Vol. 89, 636–642, 1994, herein incorporated by reference). The plant materials tested are listed in Table XI below. Herbarium specimens of each accession were collected. One accession, PS9, originally labeled as *P. macrourum,* was reclassified as *P. massaicum* [syn. *P.mezianum* Leeke (Jauhar, Cytogenetics and breeding of pearl millet and related species, Alan R. Liss, New York, 1981)]. *Pennisetum ciliare* (L.)Link is synonymous with *Cenchrus ciliaris* L.

Plant DNA was isolated as described in example 5. Inner, whorled leaf tissue was ground to a fine powder in liquid nitrogen and then added to the extraction buffer (approximately 75 ml of buffer per 10 g. tissue). Tissue was incubated in extraction buffer for 1–3 hour and subsequently processed as described above. DNA was quantified on a TKO-100 fluorometer(Hoefer Scientific Instruments, San Francisco, Calif.).

The molecular markers described above in Example 5 were used in this example. PCR reaction mixtures (50 ul) contained 50 mM Tris-HCl (pH 9.0), 50 mM KCl, 1.5 mM $MgCl_2$, 0.1% Triton X-100, 100 uM each of dATP, dCTP, dGTP, and dTTP, 0.5 uM of each primer, 25 ng genomic DNA and 0.5 U Taq DNA polymerase (Promega Corp., Madison, Wis.). Cycling was performed on a Perkin-Elmer/Cetus DNA Thermal Cycler (Norwalk, Conn.) programmed as follows for primer OPC-04 (Operon Technologies, Alameda, Calif., 5'CCGCATCTAC 3', SEQ ID NO 7): 3 cycles of 1 minute at 97° C., 1 minute at 42° C., and 2 minute at 72° C. with 3 seconds auto-segment extension of each cycle. The cycling parameters for STS marker UGT197 (synthesized by the Molecular Genetics Facility, University of Georgia; forward primer 5" CTGCAGACCTCCAAACAG 3', SEQ ID NO 3; reverse primer 5' CTGCAGCATGTGAACCAT 3', SEQ ID NO 4) were 3 cycles of 1 minute at 97° C., 1 minute at 55° C., and 2 minute at 72° C.; followed by 32 cycles of 1 minute at 94° C., 30 seconds at 55° C., and 30 seconds at 72° C. with a 3 second auto-segment extension of each cycle.

PCR-amplified DNA was electrophoresed in 2% NuSeive:SeaKEm 1:1 agarose (FMC Corp., Rockland, Me.) in 1×TBE. Genomic DNA was digested with DraI (Promega Corp., Madison, Wis.) according to the manufacturer's instructions and was electrophoresed in 0.8% SeaKem agarose in 1×TBE. DNA was transferred to nylon membrane (Genescreen Plus, NEN, DuPont, Boston, Mass.) according to the manufacturer's instructions. $OPC04_{600}$ was cloned from PS26, a *P. squamulatum* germplasm introduction, using the pGEM-T vector system (Promega Corp., Madison, Wis.) according to the manufacturer's instructions. Southern blots of DraI-digested genomic DNA were hybridized with radiolabelled cloned $OPC04_{600}$ that was PCR amplified from plasmid using M13 and M13r primers. Gel-purified UGT197 insert was radiolabelled and hybridized to Southern blots of both DraI-digested genomic DNA and DNA amplified with UGT197 STS primers. Probes were radiolabelled with [$^{32}P$] by the random hexamer method according to the manufacturer's instructions (BRL, Gaithersburg, Md. and Promega Corp., Madison, Wis.). Southern blots were prehybridized and hybridized at 65° C. in 6×SSPE, 1% SDS, and 50 ug/ml sheared salmon sperm DNA (50 ml prehyridizatrion solution/400 $cm^2$ membrane reduced to 20 ml fresh solution/400 $cm^2$ for hybridization). Hybridized blots were washed at a final stringency of 0.1×SSPE with 1% SDS at 65° C. for 30 minutes.

PCR amplification of DNA using RAPD primer OPCO4 produced numerous DNA fragments from the sexual and apomictic Pennisetum species as detected on an ethidium bromide-stained gel. Many of the species displayed amplified fragments comparable in size to the $OPC04_{600}$ of *P. squamulatum*. Size comparison alone was misleading since hybridization of a genomic Southern blot showed that the species with DNA homologous to cloned $C04_{600}$ were fewer than those implied by the comparison of band sizes in the ethidium bromide-stained gel. Three of the apomictic species, *P. squamulatum, P. ciliare,* and *P. massaicum,* showed both strong amplification with the OPC04 primer and strong homology with cloned $C4_{600}$.

Single-to-low DNA copy number in the above apomictic subset was indicated when cloned $C4_{600}$ was used as a probe on a genomic Southern blot, whereas there was an apparent dispersed repeat pattern in the subset as well as in *P. glaucum, P. purpureum,* and some other Pennisetum species when $OPC04_{600}$ amplified from *P. squamulatum* was excised out of a gel and used as a radiolabelled probe(data not shown). It appears that co-migrating DNA sequences were responsible for the dispersed repeat pattern. Williams et al. (1990, supra) and Paran et al. (Genome, Vol. 34, 1021–1026, 1991) have used excised RAPD bands as the source for their hybridization probes. Both noted hybridization patterns consistent with repetitive DNA, which prevented the use of some RAPD fragments as hybridization probes for RFLPs. Paran et al. (Theor. Appl. Genet., Vol. 85, 985–993, 1993) frequently found that DNA sequences other than the informative and predominant sequence were cloned from an excised band. It is apparent from the above results that excised RAPD bands used as RFLP probes can produce misleading hybridization patterns.

PCR amplification of DNA from the sexual and apomictic Pennisetum species using UGT197 STS primers showed an intense band of the size predicted from a known DNA sequence (144 bp, Example 5 above) from all apomictic Pennisetum species except for those in the section Brevivalvula (*P. pedicellatum, P. polystachyon,* and *P. subangustum*). Hybridization of UGT197 to a Southern blot of the PCR-amplified products verified that the PCR products were homologous to the DNA clone. In some sexual Pennisetum species, very faint amplification products of about 144 bp were detected after excessive overexposure of the autoradiogram. These faint autoradiographic bands have had a visible counterpart on a stained gel only once with *P. nervosum*. In example 5 above, it is shown that UGT197 hybridized to genomic DNA of *P. squamulatum* and $BC_3$ but not to that of *P. glaucum* or *P. purpureum*. The banding pattern and intensity of hybridization in example 5 suggests that UGT197 is single-copy DNA, Slight contamination of the DNA between samples could account for the appearance of faint bands; however, the presence of bands persisted with new reagents for PCR amplification, and the bands were not consistently amplified from one PCR amplification run to the next using the same DNA source. Contamination during isolation of the DNA should not have occurred because the items used for DNA extraction were either disposed of or autoclaved after each sample had been processed.

UGT197 did not hybridize to DraI-digested genomic DNA from sexual Pennisetum species, whereas it did hybridize to genomic DNA from all apomictic species that showed the intense PCR-amplified UGT197 STS. All of the other apomictic species except *P. ciliare* had a single band roughly comparable in size (2.8 kb) to the original source of the probe, *P. squamulatum*. *P. ciliare* had two DraI fragments, one at 5.1 kb and one at 2.4 kb. The single band in *P. flaccidum* and *P. orientate* consistently appeared slightly smaller (2.7 kb) than the single band in the *P. squamulatum*-type species (*P. massaicum, P. macrourum, P. setaceum, P. squamulatum,* and *P. villosum*). UGT197 did not hybridize with genomic DNA from the apomictic species in the section Brevivalvula, which confirms the absence of UGT197 STS in these species.

The apomictic species could be separated into four groups based on their banding pattern for UGT197: the section Brevivalvula (no hybridization), *P. flaccidum* and *P. orientale* (2.7-kb band), *P. ciliare* (two bands), and the *P. squamulatum*-type apomicts (2.8-kb band).

This example demonstrates that the two markers isolated from the apomict *P. squamulatum* are specific for apomictic species in Pennisetum.

A 537 base pair sequence and a 337 base pair sequence of linear DNA with the following sequences:

LMDA197.1n

| | | | | | | |
|---|---|---|---|---|---|---|
| SEQ ID NO 11 | 1 | ACTCNCCATC | TCTCGNTCGT | NGNCTGTCCC | CCCCCTCCCC | CACCAGGAAA |
| | | TGAGNGGTAG | ACAGCNAGCA | NCNGACAGGG | GGGGGAGGGG | GTGGTCCTTT |
| | 51 | AAGGGGGATN | TACTAAACNT | CGNNNTATGG | AGTCGANGAA | ANNCAAGTTC |
| | | TTCCCCCTAN | ATGATTTGNA | GCNNNATACC | TCAGCTNCTT | TNNGTTCAAG |
| | 101 | CTCNCGGAGC | TCTTTCAGNT | CGCGTCGACT | CCGTCGANCG | TAGCCGTCGC |
| | | GAGNGCCTCG | AGAAAGTCNA | GCGCAGCTGA | GGCAGCTNGC | ATCGGCAGCG |
| | 151 | NCCNCCCCCT | CCTCCTNCTG | CAGACCTCCA | AACAGCACGT | CCTCGAGCGC |
| | | NGGNGGGGGA | GGAGGANGAC | GTCTGGAGGT | TTGTCGTGCA | GGAGCTCGCG |
| | 201 | GGCGCGGAGG | CCCACCGCGA | TGGAACCTCG | TCTGTGGAAG | CAACGGCGGT |
| | | CCGCGCCTCC | GGGTGGCGCT | ACCTTGGAGC | AGACACCTTC | GTTGCCGCCA |
| | 251 | AGTGATAACT | GCCAGCGGCT | TATTTTATTT | GTTTCAACAG | TCCATGGTTC |
| | | TCACTATTGA | CGGTCGCCGA | ATAAAATAAA | CAAAGTTGTC | AGGTACCAAG |
| | 301 | ACATGCTGCA | GACCGNTCGC | ATTTTGCCTC | TGACAACGAC | GGTGCGGCTG |
| | | TGTACGACGT | CTGGCNAGCG | TAAAACGGAG | ACTGTTGCTG | CCACGCCGAC |
| | 351 | CCACTATGGT | TATGGTTCAG | TACAACCGAA | CCATACTCTC | CCTCGGTTCG |
| | | GGTGATACCA | ATACCAAGTC | ATGTTGGCTT | GGTATGAGAG | GGAGCCAAGC |
| | 401 | TCCACGGCGG | GTGCTCGCAT | CACATCACAA | CGGATGAATA | AAACGGTGTT |
| | | AGGTGCCGCC | CACGAGCGTA | GTGTAGTGTT | GCCTACTTAT | TTTGCCACAA |

-continued

```
              451 GGGAGANTNG  GTGCTACTCG  ATCATGACTT  GCTTGGGCAG  AACGCATCCG
                  CCCTCTNANC  CACGATGAGC  TAGTACTGAA  CGAACCCGTC  TTGCGTAGGC
              501 NGTGCTTTAC  ATAACCGGAC  AAGTTAACTT  TTACCGC
                  NCACGAAATG  TATTGGCCTG  TTCAATTGAA  AATGGCG     SEQ ID NO 13
                                     sp6.1n

SEQ ID NO 12    1 CTCGATCATC  GGGCCTTTGT  GATGCTCATG  GAGGAGATAT  ATTTATAGAG
                  GAGCTAGTAG  CCCGGAAACA  CTACGAGTAC  CTCCTCTATA  TAAATATCTC
               51 GTAAACATCG  AATAAATGGC  ATTACTGATG  TCCGTAAAAC  ATGGATGGGC
                  CATTTGTAGC  TTATTTACCG  TAATGACTAC  AGGCATTTTG  TACCTACCCG
              101 CCTTAAATGT  TGCTGACTGC  CCAACTTTTC  ACATTGAAGC  CCAAACGAGA
                  GGAATTTACA  ACGACTGACG  GGTTGAAAAG  TGTAACTTCG  GGTTTGCTCT
              151 CAAAAGCTCA  GGCCCGTTAA  CACTTTCTTT  TATAGTGCCC  ATTAACACTT
                  GTTTTCGAGT  CCGGGCAATT  GTGAAAGAAAA ATATCACGGG  TAATTGTGAA
              201 TTGGTTGCAA  GAACAACCGC  ACAAGTGAGA  GAAGGAAGGC  CAAATTTCAG
                  AACCAACGTT  CTTGTTGGCG  TGTTCACTCT  CTTCCTTCCG  GTTTAAAGTC
              251 CTTACACTAC  TGGAATCCGT  GTCAAGTTCT  TACGGCCATT  AAAATATTTT
                  GAATGTGATG  ACCTTAGGCA  CAGTTCAAGA  ATGCCGGTAA  TTTTATAAAA
              301 ACAGCATCTT  TTGTGATATA  GTACACGCAG  ATCCTAC
                  TGTCGTAGAA  AACACTATAT  CATGTGCGTC  TAGGATG     SEQ ID NO 14
```

have been sequenced from a clone recovered from a $BC_3$ genomic library cloned into the vector lambda GEM-12. The $BC_3$ genomic DNA was partially digested using Sau3A1 and the restricted DNA was size selected for 9–23 kb then partially filled in using Klenow DNA polymerase and dGTP and dATP. The DNA inserts were ligated into the partially filled in XhoI sites of the lambda GEM-12 XhoI half site arms (Promega). A DNA clone containing RFLP UGT197 was isolated using DNA-DNA hybridization of ugt197 to plaque lifts of lambda phage. The lambda clone was purified after the third such screening. DNA was isolated from the single positive lambda clone. Limited DNA regions from the lambda clone have been sequenced using the polymerase chain reaction and primers specific to one vector arm (to give the Sp6.ln sequence) or inverse primers targeting the UGT197 RFLP sequence (lmda197.ln) This region of DNA sequence is unique to apomicts in the genus Pennisetum as judged by DNA-DNA hybridization at conditions of high stringency.

TABLE 11

Accession descriptions for the plants used in this experiment grown at the Coastal Plain Experiment Station (CPES)

| CPES designation | Species | Taxonomic section[3] | Reproductive behavior | Source of plant material |
|---|---|---|---|---|
| PS938 | *P. alopecuroides* (l.) Spreng. | Not Assigned | Sexual[b] | Mary Meyer |
| PS2 | *P. basedowii* Summerhayes & Hubbard | Not Assigned | Sexual[c] | P1257782 |
| Tift23BE | *P. glaucum* (L.) R. Br. | Penicillaria | Sexual[d] | CPES-UGA |
| PS156 | *P. hohenackeri* Hochst. ex Steud. | Gymnothrix | Sexual[e] | ICRISAT |
| PS38 | *P. nervosum* (Nees) Trin. | Not Assigned | Sexual[b] | Mexico |
| PS187 | *P. nervosum* (Nees) Trin. | Not Assigned | Sexual[b] | Argentina |
| N109 | *P. purpureum* Schumach | Penicillaria | Sexual[f] | Spain |
| N168 | *P. purpureum* Schumach | Penicillaria | Sexual[f] | Kenya (I brahim) |
| PS29 | *P. ramosum* (Hochst.) Schweinf. | Gymnothrix | Sexual[e] | P13311699 |
| PS63 | *P. ramosum* (Hochst.) Schweinf. | Gymnothrix | Sexual[e] | DeWet & Harlan |
| PS243 | *P. schweinfurthii* Pilger | Heterostachya | Sexual[b] | ICRISAT (IP8627) |
| PS163 | *P. subangustum* (Schum.) Stapf. & Hubb | Brevivalvula | Apospory[b] | Nigeria |
| PS185 | *P. ciliare* (L.) Link | Not Assigned | Apospory[g] | Llano |
| PS186 | *P. ciliare* (L.) Link | Not Assigned | Apospory[g] | Nueces |
| PS32 | *P. flaccicum* Griseb. | Not Assigned | Apospory[h] | PI271601 |
| PS95 | *P. flaccidum* Griseb. | Not Assigned | Apospory[h] | Dr. Timothy |
| PS9 | *P. massaicum* Stapf | Gymnothrix | Apospory[h] | PI365021 |
| PS962 | *P. macrourum* Trin. | Not Assigned | Apospory[c] | Zimbabwe |
| PS12 | *P. orientale* L.C. Rich | Not Assigned | Apospory[j] | PI315867 |
| PS13 | *P. orientale* L.C. Rich | Not Assigned | Apospory[j] | PI218097 |
| PS16 | *P. pedicellatum* Trin. | Brevivalvula | Apospory[k] | PI266185 |
| PS304 | *P. pedicellatum* Trin. | Brevivalvula | Apospory[k] | Senegal (Harlan) |
| PS19 | *P. polystachyon* (L.) Shult. | Brevivalvula | Apospory[c] | PI189347 |
| PS264 | *P. polystachyon* (L.) Shult. | Brevivalvula | Apospory[c] | PI284770 |
| PS22 | *P. setaceum* (Forsk.) Chiov. | Eu-pennisetum | Apospory[e] | PI300087 |
| PS25 | *P. setaceum* (Forsk.) Chiov. | Eu-pennisetum | Apospory[e] | PI364994 |
| PS24 | *P. squamulatum* Fresen | Heterostachya | Apospory[c] | PI248534 |

TABLE 11-continued

Accession descriptions for the plants used in this experiment grown at the Coastal Plain Experiment Station (CPES)

| CPES designation | Species | Taxonomic section[3] | Reproductive behavior | Source of plant material |
|---|---|---|---|---|
| PS158 | *P. squamulatum* Fresen | Heterostachya | Apospory[c] | ICRISAT |
| PS249 | *P. villosum* R. Br. ex Fresen | Eu-pennisetum | Apospory[e] | Israel |

[a]Stapf and Hubbard, all species have not been put into a section
[b]unpublished data
[c]Dujardin and Hanna 1984
[d]Brunken et al. 1977
[e]Narayan 1962
[f]Hanna 1981
[g]Snyder et al. 1955
[h]Chatterji and Timothy 1969a
[i]r,'Cruz and Reddy 1968
[j]Chatterji and Timothy 1969b
[k]Kalyane and Chatterji 1981

Example 7

The $F_1$hybrid population from the cross between tetraploid pearl millet and *P. squamulatum* is used for developing a relative genetic mnap of the apomixis linkage group (FIG. 1). Relative mnap units are shown on the left of the vertical lines and specific loci are shown to the right. Markers UGT197, C4, U12H, R13, A14M, M2M, 07M, W10M, X19H, and Y11H all show no recombination with the apomixis locus in our present population of 84 individuals. Markers C4, U12H, R13, A14M, M2M, 07M, W10M, X19H, and Y11H are derived from RAPD fragments that were isolated by their presence in the DNA from a pool of 16 $F_1$ apomictic individuals (apomictic bulk) and their absence in a pool of 16 $F_1$ sexual individuals (sexual bulk). Segregation in the total population was determined by assaying each marker separately on each of the 84 individuals. Each marker ending in a letter was isolated from DNA bulks where the DNA had been digested with MspI (M) or HaeIII (H) prior to performing the RAPD reactions.

Example 8

A $BC_4$generation of progenies is developed to transfer genes controlling apomixis while reducing alien chromosomes (Hanna et al, J. of Heredity, Vol. 84(3), 213–216, 1993, herein incorporated by reference). A tetraploid (2n=4x=28) pearl millet, K174, a fertile derivative from a tetraploid Tift 239DB×tetraploid Tift 23BE cross, as the recurrent parent (Dujardin et al, Euphytica, Vol. 42, 285–289, 1989), is used as the female or seed parent to produce $BC_4$ progenies. Inflorescences of K174 pearl millet are bagged with glassine bags before stigma exsertion. After the stigmas exserted (pearl millet has a protogynous habit of flowering), the stigmas are dusted with pollen from K169-46 plants as described above in example 3. Plant A190 was recovered from an A22 ($BC_4$ facultative apomict)×A17 ($BC_4$ facultative apomict) cross from which one plant was established. Chromosome behavior and embryo sac development was determined using the three $BC_4$plants- A22, A25, and A190- which exhibit the highest frequency of aposporous embryo sac development. Development of embryo sacs is studied in the open-pollinated (OP) and selfed progenies of seven $BC_4$ plants: A1, A4, A17, A19, A22, and A25. Meiosis is studied in young inflorescences fixed in a 9:3:1 solution of absolute alcohol, chloroform, and acetic acid for 24 h and stored in 70% ethanol. Chromosomes are stained in 1% acetcarmine. Embryo sac development is studied in inflorescences fixed in FAA. Ovaries are dehydrated in tertiary butyl alcohol, sectioned at 12 um, and stained in safranin-0 fast green, or observed cleared with methyl salicylate (Young et al., Can J Bot, Vol 57, 1678–1672, 1979) with a phase microscope.

A molecular marker shown to cosegregate with apomixis in the $BC_4$ progeny is used to test eight randomly selected progeny of A22, A25, and A190. The marker, a sequence tagged site, was amplified by the polymerase chain reaction (PCR) using conditions described in example 5, above, except that annealing temperature is increased to 55° C. Pollen fertility is estimated by determining the percentage pollen stainability with $I_2KI$. At least 300 pollen grains were observed from each plant. The number of spikelets per cm of inflorescence was determined on the center section of three inflorescences from each of A22, A190, k174 (pearl millet), and K169-46 ($BC_3$, example 4 above) and one inflorescence of A25. Seed set was determined on 10 inflorescences from each plant.

The transfer frequency of gene(s) controlling apomixis through the pollen has been low (<5%) in advanced BC generations (Dujardin et al. J. Genet. Breed., Vol. 43, 145–151, 1989); however, nine plants were identified with apomictic embryo sac development. Viable seeds were obtained and progenies were established from seven of these plants (See Table XII below).

$BC_4$ plants more closely resemble tetraploid cultivated pearl millet (the recurrent parent) in leaf, stem, and inflorescence characteristics than the K169-46 $BC_3$ plant used as the male parent. Inflorescences of $BC_4$ plants are more compact, ranging from 243 (A25) to 398±72 (A22) spikelets per 5 cm of inflorescence, compared to 482±62 for tetraploid pearl millet and 161±27 for the $BC_3$ plants. There is a loss of the sparse arrangement of spikelets from the $BC_3$ to $BC_4$generations which indicates that there is a loss of chromosomes and/or gene(s) derived from the wild species, *P. squamulatum* and/or *P. purpureum*. Plant heights are 1.8±0.1, 1.6±0.2, 1.4 (only one plant), 1.5±0.2, and 1.2±0.1 m for A22, A25, A190, K174 (4×pearl millet), and K169-46 ($BC_3$) plants, respectively. Inflorescence lengths average 22±2, 22±1, 20±2, 21±3, and 9±1 cm for A22, A25, A190, K174, and K169-46, respectively.

Somatic chromosome numbers in A22, A25, and A190 are 2n=29,27, and 28 plus a telocentric fragment, respectively. The telocentric fragment of A190 apparently arose from misdivision of a chromosome in either A22 or A17. The range in chromosome numbers observed in the $BC_4$ generation is similar to that in the $BC_3$ generations (Dujardin et al., J. Genet. Breed., Vol.43, 145–151, 1989).

Observations of metaphase I chromosome pairing (see Table XIII below) indicate that, on the average, chromosomes of $BC_4$ plants formed one more bivalent and two less univalents than chromosomes of the $BC_3$ parent. Previous research shows 9.76 (Dujardin et al., Euphyta, Vol. 42, 285–289, 1989) and 8.97 (Hanna et al., Can. J. Genet. Cytol., Vol. 18, 529–536, 1976) bivalents for tetraploid pearl millet. The smaller number of bivalents and quadrivalents and the larger number of univalents and trivalents in $BC_4$ plants compared to tetraploid pearl millet suggests that $BC_4$ may still have two to five chromosomes of the wild species, some of which have gene(s) controlling apomixis. Example 5, above, indicates that $BC_3$ plants have at least two alien chromosomes that assort independently in $BC_4$. The higher number of bivalents and fewer univalents observed in $BC_4$ than in $BC_3$ plants also indicates that the $BC_4$ plants have fewer alien chromosomes than the $BC_3$ plant.

Chromosome segregation at anaphase I is irregular, with as many as 16 and as few as 11 chromosomes migrating to a pole. A limited number of laggards are also observed. Behavior of the telocentric fragment in A190 is not included in the data in Table XIII below. It remained nonassociated in 60% of the microsporocytes and associated with a univalent or bivalent in 14% and 26% of the microsporocytes, respectively.

Ovules of $BC_4$ plants A22 and A190 (a derivative of A22) show a high frequency of aposporous embryo sacs (Table XIV below). Four of 36 progeny from A22 were morphologically variable. Twelve percent of the ovules of A25 had single sexual embryo sacs, which probably accounts for part of the 19% morphologically variable progeny from this plant (Table XII below).

Progenies of $BC_4$ plants that have a high frequency of ovules with sexual embryo sacs and/or show a facultative behavior (A1, A4, A7, A17, and A19) also are morphologically variable (Table XII below).

Four (A1, A7, A17, and A19) of the seven $BC_4$ plants produce only morphologically variable progenies, while three $BC_4$ plants produce from 50%(A4) to 89% (A22) uniform maternal types (See Table XII). A large portion of the OP progenies from the four $BC_4$ plants that produce only variable progenies show only a aposporous embryo sac development, indicating some recombination in the $BC_4$ plants to produce new apomictic genotypes. Selfing could have occurred in a facultative apomictic even though the inflorescences were not bagged, or the addition of modifiers and/or genes for apomixis could have been added from an unknown apomictic parent (pollinator) that was flowering near the $BC_4$ plants. These modifiers and/or genes controlling apomixis could immediately express themselves in these progenies, since apomixis appears to be dominant in these crosses.

Pollen stainability is 23% for A22, 32% for A25, and 10% for A190. Plants with the highest frequency of apomictic reproduction, A22 and A190, have the lowest pollen stainability. The lower pollen stainability in these apomicts is probably caused by the presence of alien chromatin.

TABLE 12

Embryo sac classification and morpholobical variation of progenies from self and open-pollination (OP) of $BC_4$ Plants

| $BC_4$ plant | Type of pollination | No. of progeny: Reproductive mode* AP | Facul | Sex | Morphological type Maternal | Other |
|---|---|---|---|---|---|---|
| A1 | OP | 8 | 19 | 18 | 0 | 45 |
| A4 | OP | 10 | 4 | 4 | 9 | 9 |
| A7 | OP | 11 | 7 | 10 | 0 | 28 |
| A17 | OP | 0 | 5 | 5 | 0 | 10 |
| A19 | OP | 2 | 4 | 4 | 0 | 10 |
| A22 | Selfed | 6 | 0 | 1 | 6 | 1 |
| | OP | 24 | 5 | 0 | 26 | 3 |
| A25 | Selfed | 5 | 10 | 4 | 14 | 5 |
| | OP | 6 | 9 | 3 | 16 | 2 |

*Observation on individual plants in $BC_4$ progenies.

AP = only aposporous sacs in ovules; Facul = facultative, with both aposporous and sexual sacs; Sex = only sexual sacs in ovules.

TABLE 13

Metaphase I chromosome associations in tetraploid (4x) pearl millet and $BC_3$ and $BC_4$ derivatives

| Plant No. | No. of PMCs* | No. Chromosomes | Metaphase I chromosome associations I | II | III | IV |
|---|---|---|---|---|---|---|
| $BC_3$ | | | | | | |
| K169-46[h] | 106 | 29 | 9.33 | 5.86 | 1.74 | 0.65 |
| Range | | | (5–13) | (2–10) | (0–6) | (0–3) |
| $BC_4$ | | | | | | |
| A22 | 90 | 29 | 8.64 | 6.70 | 1.18 | 0.82 |
| Range | | | (1–15) | (3–11) | (0–4) | (0–4) |
| A25 | 90 | 27 | 6.39 | 6.15 | 1.80 | 0.80 |
| Range | | | (1–13) | (1–12) | (0–6) | (0–4) |
| A190 | 90 | 28+ | 6.88 | 7.29 | 1.14 | 0.75 |

TABLE 13-continued

Metaphase I chromosome associations in tetraploid (4x) pearl millet and $BC_3$ and $BC_4$ derivatives

| Plant No. | No. of PMCs* | No. Chromosomes | Metaphase I chromosome associations I | II | III | IV |
|---|---|---|---|---|---|---|
| Range | | | (0–15) | (2–12) | (0–5) | (0–3) |
| K174 Pearl Millet | | | | | | |
| (4x)[4] | 690 | 28 | 2.64 | 8.96 | 0.38 | 1.49 |
| Range | | | (0–14) | (0–14) | (0–5) | (0–6) |

PMC = pollen mother cells
Data from Dujardin and Hanna (1989a)
Probably 28 chromosomes plus a telocentric fragment (telocentric fragment association not included in these data but discussed in text)
Data from Hanna et al. (1976)

TABLE 14

Embryo sac development in ovules from $BC_4$ plants

| Plant | No. of | No. of ovules according to embryo sac type* AP | Facul | Sex | Ab |
|---|---|---|---|---|---|
| A22 | 56 | 54 | 1 | 1 | |
| A25 | 91 | 55 | 14 | 11 | 11 |
| A190 | 88 | 83 | 1 | 1 | 3 |

*AP = only aposporous sacs in ovules; Facul = facultative with both asposporous and sexual sacs; Sex = only sexual sacs in ovules; Ab = only aborted sacs.

Seed set in the apomictic plants, A22 , A25, and A190 is almost 100% until days 11 or 12, at which time developing seeds abort. Final seed set for A22 is 16% compared to 3% for A25 and A190. The low seed set for A25 and A190 is similar to that observed on K169-46, the apomictic $BC_3$ plant.

Morphologically, the $BC_4$ plants closely resemble pearl millet, which indicates a loss of alien chromosomes from *P. squamulatum* and *P. purpureum*. A highly apomictic plant along with plants with varying degrees of sexual development are recovered in the $BC_4$ generation. It appears that some of the apomictic behavior has been lost in the $BC_4$ previous generations previous generations. The facultative behavior in $BC_4$ could be due to loss of genes (or chromosomes) controlling apomixis, loss of modifiers, and/or effects of genetic background, since more of the sexual *P. glaucum* genetic background is probably represented in the $BC_4$ plants.

Example 9

The backcross procedure of examples 3 and 7 are repeated to produce backcross 5 and backcross 6 generations. In each generation, plants are selected for partial male fertility (viable pollen shed) and apomictic development as well as improved seed set. Plant A22 described above, in Example 7, is used to pollinate tetraploid pearl millet K174 (2n=4X=28) using the method described in Example 7 above. A plant progeny with a high frequency of aposporous apomictic embryo sacs and partial male fertility was selected. This plant, plant B687-2-14, was used to develop open-pollinated progeny C190. C190 was used to pollinate a new induced tetraploid pearl millet of inbred Tift 8677 to select a hybrid with a high frequency of aposporous apomictic embryo sacs and partial male fertility using methods described in the above examples. Seeds of diploid (2N=2X=214) TIFT 8677 were placed on germination pads moistened with distilled water for 12 hours at which time seeds were placed in a 0.1% solution of colchicine for 6 hours. Seeds were then rinsed in running tap water for 30 minutes and transplanted to steam sterilized soil. Six centimeter tall seedlings were transplanted to 5 cm pots. At three weeks after transplanting, plants were transplanted to the field. Tetraploid plants were identified by robust stigmas and confirmed by somatic chromosome and/or meiotic chromosome counts. Hybrid D16-479 was selected and progeny from seeds from open-pollinated inflorescences of D16-479 produced 95% maternal types and was designated E111. Morphological characteristics of aposporous apomictic E111, cultivated tetraploid (2n=4x=28) pearl millet (recurrent parent in backcrossing process) and *Pennisetum squamulatum* (2n=6x=54 chromosome aposporous apomictic species donating the apomictic mechanism) are summarized in Table XV below (See also FIGS. 2–7). The data in Table XV and FIGS. 11–16 show that E111 is morphologically intermediate to cultivated pearl millet and *P. squamulatum*. FIGS. 11 and 12 are E111, FIGS. 13 and 14 are tetraploid cultivated sexual pearl millet, and FIGS. 15 and 16 are apomictic *Pennisetum squamulatum*. However, the data for the 'number of spikelets per 2.5 cm of inflorescence' and 'flag leaf width' (two characteristics showing the most variation between pearl millet and *P. squamulatum*) indicate that E111 more closely resembles cultivated tetraploid pearl millet (the recurrent or recipient plant) than the wild *P. squamulatum,* the species donating the apomixis mechanism.

Cytological observations on 100 ovules at anthesis from E111 showed that five ovules aborted. Of the remaining 95 ovules, seven had only one sexual embryo sac, four had one sexual embryo sac plus one or two aposporous apomictic embryo sacs and 84 had one or more aposporous embryo sacs. Ovules with aposporous embryo sacs averaged 2.4–1.1 sacs per ovule with a range from one to six embryo sacs per ovule.

Roottip chromosome counts show that E111 has 2n=29 chromosomes. Tetraploid cultivated pearl millet has 2n=4x=28 chromosomes and has been the recurrent parent in the backcross process.

TABLE 15

Morphological characteristics of aposporous apomictic E111, tetraploid (4x) pearl millet and *Pennisetum squamulatum* (the donor species)

| Characteristic measured | Plant Identity | | |
|---|---|---|---|
| | E111 | 4x Pearl millet | *Pennisetum squamulatum* |
| Plant height (cm) | | | |
| x ± SD | 161 ± 7 (51)[A] | 141 ± 14 (31) | 151 ± 15 (14) |
| Range | 148–180 | 110–175 | 127–180 |
| Flag leaf width (cm) | | | |
| x ± SD | 3.1 ± 0.3 (51) | 3.1 ± 0.5 (31) | 0.7 ± 0.2 (9) |
| Range | 2.2–3.6 | 2.1–4.5 | 0.5–1.0 |
| Inflorescence length (cm) | | | |
| x ± SD | 28 ± 2 (51) | 22 ± 3 (31) | 27 ± 2 (13) |
| Range | 23–31 | 14–26 | 23–30 |
| Number spikelets per 2.5 cm inflorescence | | | |
| x ± SD | 147 ± 24 (11) | 182 ± 34 (12) | 43 ± 9 (7) |
| Range | 103–191 | 130–242 | 34–61 |

[A]number in parenthesis is the number of plants measured.

Two hundred pollen grains were observed from each of three E111 maternal plants. Of the 600 pollen grains observed, 153 or 25% appeared normal with starch grains. 75% of the pollen grains were aborted, shriveled or collapsed. There is enough male fertility present in E111 to transfer the aposporous apomictic mechanism in sexual× apomictic crosses to produce commercial $F_1$ apomictic hybrids and/or transfer the apomictic mechanism to other genotypes.

Eighty-six plants established in 1995 at Tifton, Ga. from seed produced from open-pollination of E111 (selected as 16–479) in the apomixis crossing and selection nursery produced 82 maternal and 4 offtype progenies or 95% maternal progeny. This indicates that a high level of apomixis has been maintained in E111 to the backcross-6 (BC6) generation.

The present invention is not limited in scope by the seeds deposited, since the deposited elements are intended as single illustrations of one aspect of the invention and any seeds, cell lines, plant parts, plants derived from tissue culture or seeds which are functionally equivalent are within the scope of this invention.

The foregoing detailed description is for the purpose of illustration. Such detail is solely for that purpose and those skilled in the art can make variations therein without departing from the spirit and scope of the invention.

We claim:

1. A cultivated apomictic Pennisetum plant comprising a genome which contains a genetic material from E111, designated by ATCC accession No. 97273, for the expression of apomixis, wherein said material is transferred from *Pennisetum squamulatum.*

2. An apomictic pearl millet plant comprising a genome which contains a genetic material from E111, designated by ATCC accession No. 97273, for the expression of apomixis, wherein said material is transferred from *Pennisetum squamulatum.*

3. A seed resulting from a cross of the plant of claim 1 with a nurse cultivar.

4. A seed resulting from a cross of the plant of claim 2 with a nurse cultivar.

5. A progeny plant produced by the seed of claim 3.

6. A progeny plant produced by the seed of claim 4.

7. The plant of claim 1 wherein said genetic material is identifiable by linkage to a molecular marker selected from the group consisting of SEQ ID NO 11 and SEQ ID NO 12.

8. The plant of claim 2 wherein said genetic material is identifiable by linkage to a molecular marker selected from the group consisting of SEQ ID NO 11 and SEQ ID NO 12.

9. A cultivated apomicitic Pennisetum plant comprising a genome which contains a genetic material from E111, designated by ATCC No. 97273, for the expression of apomixis, wherein said material is transferred from *Pennisetum squamulatum* and is identifiable by linkage to a molecular marker selected from the group consisting of SEQ ID NO 11 and SEQ ID NO 12.

10. A cultivated Pennisetum plant comprising a dominant genetic mechanism from E111, designated by ATCC accession No. 97273, responsible for chromosomal non-reduction in embryo sacs.

11. A cultivated Pennisetum plant comprising a dominant genetic mechanism from E111, designated by ATCC accession No. 97273, responsible for aposporous apomictic opment of an unreduced egg in *Pennisetum squamulatum.*

* * * * *

UNITED STATES PATENT AND TRADEMARK OFFICE

CERTIFICATE OF CORRECTION

PATENT NO. : 5,811,636

DATED : September 22, 1998

INVENTOR(S) : Wayne W. Hanna, Peggy Ozias-Akins and Michel Dujardin

It is certified that error appears in the above-identified patent and that said Letters Patent is hereby corrected as shown below:

On the title page, item [73]:

Please correct the Assignee to include:

The University of Georgia Research Foundation, Inc.
Athens, Georgia

Signed and Sealed this

Twenty-sixth Day of October, 1999

*Attest:*

Q. TODD DICKINSON

*Attesting Officer*

*Acting Commissioner of Patents and Trademarks*